US010660753B2

(12) United States Patent
Pham et al.

(10) Patent No.: US 10,660,753 B2
(45) Date of Patent: May 26, 2020

(54) LEAFLET CAPTURE AND ANCHOR DEPLOYMENT SYSTEM

(71) Applicant: Pipeline Medical Technologies, Inc., Santa Rosa, CA (US)

(72) Inventors: Trung Ho Pham, Santa Rosa, CA (US); Gordon B. Bishop, Santa Rosa, CA (US); Erik Griswold, Penngrove, CA (US); Stephen McDaniel, San Rafael, CA (US); Cameron Paul Purcell, Santa Rosa, CA (US)

(73) Assignee: Pipeline Medical Techologies, Inc., Santa Rosa, CA (US)

( * ) Notice: Subject to any disclaimer, the term of this patent is extended or adjusted under 35 U.S.C. 154(b) by 0 days.

(21) Appl. No.: 16/509,230

(22) Filed: Jul. 11, 2019

(65) Prior Publication Data
US 2019/0328527 A1    Oct. 31, 2019

Related U.S. Application Data

(63) Continuation of application No. 16/297,422, filed on Mar. 8, 2019, which is a continuation-in-part of (Continued)

(51) Int. Cl.
*A61F 2/24* (2006.01)
*A61B 17/04* (2006.01)
(Continued)

(52) U.S. Cl.
CPC ........ *A61F 2/2457* (2013.01); *A61B 17/0401* (2013.01); *A61B 17/0469* (2013.01); (Continued)

(58) Field of Classification Search
CPC ................. A61F 2/2457; A61F 2/2466; A61F 2220/0075; A61F 2220/0016; (Continued)

(56) References Cited

U.S. PATENT DOCUMENTS 5,329,923 A    7/1994    Lundquist
6,269,819 B1   8/2001    Oz et al.
(Continued)

FOREIGN PATENT DOCUMENTS

EP    1 898 802    3/2008
EP    2 979 647    2/2016
(Continued)

OTHER PUBLICATIONS

Carpentier, "Cardiac valve surgery—The French Correction," 86 J of Thoracic and Cardio Surg, 323-337 (Sep. 1983).
(Continued)

*Primary Examiner* — Ashley L Fishback
(74) *Attorney, Agent, or Firm* — Knobbe, Martens, Olson & Bear, LLP

(57) ABSTRACT

Methods and devices for transvascular prosthetic chordae tendinea implantation are disclosed. A catheter is advanced into the left atrium. From an atrium side, a leaflet connector carried by a distal end of the catheter can be anchored to a superior surface of a mitral valve leaflet. A needle is axially advanceable through the leaflet connector and through the leaflet. A leaflet anchor having a leaflet suture can be advanced out of the needle to secure the mitral valve leaflet to the leaflet suture. A ventricular anchor is anchored to the wall of the ventricle to secure the ventricular wall to a ventricle suture. The leaflet suture and the ventricle suture may be tensioned and connected by a suture lock to form an artificial chordae.

17 Claims, 19 Drawing Sheets

Related U.S. Application Data application No. 15/858,671, filed on Dec. 29, 2017, which is a continuation-in-part of application No. 15/638,176, filed on Jun. 29, 2017, now Pat. No. 9,877,833.

(60) Provisional application No. 62/641,612, filed on Mar. 12, 2018, provisional application No. 62/441,031, filed on Dec. 30, 2016.

(51) Int. Cl.
*A61B 17/00* (2006.01)
*A61B 17/06* (2006.01)

(52) U.S. Cl.
CPC ........ *A61F 2/2466* (2013.01); *A61B 17/0467* (2013.01); *A61B 17/0487* (2013.01); *A61B 2017/00243* (2013.01); *A61B 2017/00783* (2013.01); *A61B 2017/0406* (2013.01); *A61B 2017/0409* (2013.01); *A61B 2017/0441* (2013.01); *A61B 2017/0464* (2013.01); *A61B 2017/0488* (2013.01); *A61B 2017/06052* (2013.01); *A61F 2220/0016* (2013.01); *A61F 2220/0075* (2013.01); *A61F 2230/0091* (2013.01)

(58) Field of Classification Search
CPC ......... A61F 2230/0091; A61B 17/0469; A61B 2017/0406; A61B 2017/0441; A61B 2017/0409; A61B 2017/0464
See application file for complete search history.

(56) References Cited

U.S. PATENT DOCUMENTS

| | | | |
|---|---|---|---|
| 6,458,107 B1 | 10/2002 | Ockuly | |
| 6,461,366 B1 | 10/2002 | Seguin | |
| 6,626,930 B1 | 9/2003 | Allen et al. | |
| 6,629,534 B1 | 10/2003 | St. Goar | |
| 6,743,239 B1 | 6/2004 | Kuehn et al. | |
| 6,752,813 B2 | 6/2004 | Goldfarb et al. | |
| 6,770,083 B2 | 8/2004 | Seguin | |
| 6,840,246 B2 | 1/2005 | Downing | |
| 6,978,176 B2 | 12/2005 | Lattouf | |
| 7,048,754 B2 | 5/2006 | Martin et al. | |
| 7,083,628 B2 | 8/2006 | Bachman | |
| 7,191,545 B2 | 3/2007 | Yi | |
| 7,226,467 B2 | 6/2007 | Lucatero et al. | |
| 7,288,097 B2 | 10/2007 | Seguin | |
| 7,464,712 B2 | 12/2008 | Oz et al. | |
| 7,563,267 B2 | 7/2009 | Goldfarb et al. | |
| 7,604,646 B2 | 10/2009 | Goldfarb et al. | |
| 7,608,091 B2 | 10/2009 | Goldfarb et al. | |
| 7,632,308 B2 | 12/2009 | Loulmet | |
| 7,635,386 B1 | 12/2009 | Gammie | |
| 7,637,903 B2 | 12/2009 | Lentz et al. | |
| 7,655,015 B2 | 2/2010 | Goldfarb et al. | |
| 7,666,204 B2 | 2/2010 | Thornton et al. | |
| 7,682,369 B2 | 3/2010 | Seguin | |
| 7,736,388 B2 | 6/2010 | Goldfarb et al. | |
| 7,871,368 B2 | 1/2011 | Zollinger et al. | |
| 7,871,433 B2 | 1/2011 | Lattouf | |
| 7,887,552 B2 | 2/2011 | Bachman | |
| 7,914,515 B2 | 3/2011 | Heideman et al. | |
| 7,914,545 B2 | 3/2011 | Ek | |
| 8,075,570 B2 | 12/2011 | Bolduc et al. | |
| 8,100,923 B2 | 1/2012 | Paraschac et al. | |
| 8,172,872 B2 | 5/2012 | Osypka | |
| 8,241,304 B2 | 8/2012 | Bachman | |
| 8,252,050 B2 | 8/2012 | Maisano et al. | |
| 8,273,054 B2 | 9/2012 | St. Germain et al. | |
| 8,303,622 B2 | 11/2012 | Alkhatib | |
| 8,409,273 B2 | 4/2013 | Thornton et al. | |
| 8,465,500 B2 | 6/2013 | Speziali | |
| 8,475,472 B2 | 7/2013 | Bachman | |
| 8,480,730 B2 | 7/2013 | Maurer et al. | |
| 8,545,551 B2 | 10/2013 | Loulmet | |
| 8,545,553 B2 | 10/2013 | Zipory et al. | |
| 8,603,066 B2 | 12/2013 | Heidman et al. | |
| 8,690,939 B2 | 4/2014 | Miller et al. | |
| 8,778,016 B2 | 7/2014 | Janovsky et al. | |
| 8,814,824 B2 | 8/2014 | Kauphusman et al. | |
| 8,852,213 B2 | 10/2014 | Gammie et al. | |
| 8,940,042 B2 | 1/2015 | Miller et al. | |
| 8,945,211 B2 | 2/2015 | Sugimoto | |
| 8,951,285 B2 | 2/2015 | Sugimoto et al. | |
| 8,951,286 B2 | 2/2015 | Sugimoto et al. | |
| 9,011,520 B2 | 4/2015 | Miller et al. | |
| 9,023,065 B2 | 5/2015 | Bolduc et al. | |
| 9,050,187 B2 | 6/2015 | Sugimoto et al. | |
| 9,131,939 B1 | 9/2015 | Call et al. | |
| 9,180,007 B2 | 11/2015 | Reich et al. | |
| 9,198,649 B2 | 12/2015 | Karapetian et al. | |
| 9,259,218 B2 | 2/2016 | Robinson | |
| 9,277,994 B2 | 3/2016 | Miller et al. | |
| 9,307,980 B2 | 4/2016 | Gilmore et al. | |
| 9,314,242 B2 | 4/2016 | Bachman | |
| 9,474,606 B2 | 10/2016 | Zipory et al. | |
| 9,492,264 B2 | 11/2016 | Fifer et al. | |
| 9,572,667 B2 | 2/2017 | Solem | |
| 9,636,205 B2 | 5/2017 | Lee et al. | |
| 9,636,224 B2 | 5/2017 | Zipory et al. | |
| 9,668,860 B2 | 6/2017 | Kudlick et al. | |
| 9,681,864 B1 | 6/2017 | Gammie et al. | |
| 9,681,964 B2 | 6/2017 | MacKenzie | |
| 9,693,865 B2 | 7/2017 | Gilmore et al. | |
| 9,724,195 B2 | 8/2017 | Goodwin et al. | |
| 9,750,493 B2 | 9/2017 | Robinson et al. | |
| 9,814,454 B2 | 11/2017 | Sugimoto et al. | |
| 9,877,833 B1 | 1/2018 | Bishop et al. | |
| 10,039,644 B2 | 8/2018 | Navia et al. | |
| 10,076,327 B2 | 9/2018 | Ellis et al. | |
| 10,130,791 B2 | 11/2018 | Heideman et al. | |
| 10,159,571 B2 | 12/2018 | de Canniere | |
| 10,206,673 B2 | 2/2019 | Maisano et al. | |
| 10,231,727 B2 | 3/2019 | Sutherland et al. | |
| 10,285,686 B2 | 5/2019 | Gammie et al. | |
| 2003/0105519 A1 | 6/2003 | Fasol et al. | |
| 2003/0120341 A1 | 6/2003 | Shennib et al. | |
| 2004/0044365 A1 | 3/2004 | Bachman | |
| 2004/0049207 A1 | 3/2004 | Goldfarb et al. | |
| 2005/0177132 A1 | 8/2005 | Lentz et al. | |
| 2005/0177180 A1 | 8/2005 | Kaganov et al. | |
| 2005/0251210 A1 | 11/2005 | Westra et al. | |
| 2007/0010857 A1* | 1/2007 | Sugimoto | A61B 17/00234 606/232 |
| 2007/0118151 A1 | 5/2007 | Davidson | |
| 2007/0123979 A1 | 5/2007 | Perier et al. | |
| 2007/0219565 A1 | 9/2007 | Saadat | |
| 2008/0177304 A1 | 7/2008 | Westra et al. | |
| 2008/0195126 A1 | 8/2008 | Solem | |
| 2008/0228165 A1 | 9/2008 | Spence et al. | |
| 2008/0228223 A1 | 9/2008 | Alkhatib | |
| 2008/0288061 A1 | 11/2008 | Maurer et al. | |
| 2009/0043153 A1 | 2/2009 | Zollinger et al. | |
| 2009/0069847 A1 | 3/2009 | Hashiba et al. | |
| 2009/0088837 A1 | 4/2009 | Gillinov et al. | |
| 2009/0287304 A1 | 11/2009 | Dahlgren et al. | |
| 2010/0023118 A1 | 1/2010 | Medlock et al. | |
| 2010/0280604 A1 | 11/2010 | Zipory et al. | |
| 2011/0011917 A1 | 1/2011 | Loulmet | |
| 2011/0022083 A1 | 1/2011 | DiMatteo et al. | |
| 2011/0040326 A1 | 2/2011 | Wei | |
| 2011/0060407 A1 | 3/2011 | Ketai et al. | |
| 2011/0301698 A1 | 12/2011 | Miller et al. | |
| 2012/0065464 A1 | 3/2012 | Ellis et al. | |
| 2012/0116418 A1 | 5/2012 | Belson et al. | |
| 2012/0172915 A1 | 7/2012 | Fifer et al. | |
| 2013/0035757 A1 | 2/2013 | Zentgraf et al. | |
| 2013/0190741 A1 | 7/2013 | Moll et al. | |
| 2013/0253639 A1 | 9/2013 | Alkhatib | |
| 2014/0142687 A1 | 5/2014 | De Canniere et al. | |
| 2014/0142689 A1 | 5/2014 | De Canniere et al. | |

(56) References Cited

U.S. PATENT DOCUMENTS

| | | |
|---|---|---|
| 2014/0243877 A9 | 8/2014 | Lee et al. |
| 2014/0243963 A1 | 8/2014 | Sheps et al. |
| 2015/0032127 A1 | 1/2015 | Gammie et al. |
| 2015/0182255 A1 | 7/2015 | Shivkumar |
| 2015/0230919 A1 | 8/2015 | Chau et al. |
| 2015/0250590 A1 | 9/2015 | Gries et al. |
| 2015/0313620 A1 | 11/2015 | Suri |
| 2015/0342737 A1 | 12/2015 | Biancucci et al. |
| 2015/0359632 A1 | 12/2015 | Navia et al. |
| 2016/0058557 A1 | 3/2016 | Reich et al. |
| 2016/0143737 A1 | 5/2016 | Zentgraf et al. |
| 2016/0192925 A1 | 7/2016 | Bachman |
| 2016/0228117 A1 | 8/2016 | Borden |
| 2016/0240941 A1 | 8/2016 | Stavrianoudakis |
| 2016/0256269 A1 | 9/2016 | Cahalane et al. |
| 2016/0310701 A1 | 10/2016 | Pai |
| 2016/0354082 A1 | 12/2016 | Oz et al. |
| 2017/0042658 A1 | 2/2017 | Lee et al. |
| 2017/0043120 A1 | 2/2017 | Heideman et al. |
| 2017/0086975 A1 | 3/2017 | Gilmore et al. |
| 2017/0119368 A1 | 5/2017 | Solem |
| 2017/0156861 A1 | 6/2017 | Longoria et al. |
| 2017/0202657 A1 | 7/2017 | Lee et al. |
| 2017/0202669 A1 | 7/2017 | Schaffner et al. |
| 2017/0252032 A1 | 9/2017 | Hiorth et al. |
| 2017/0258464 A1 | 9/2017 | Gammie et al. |
| 2017/0258588 A1 | 9/2017 | Zipory et al. |
| 2017/0258594 A1 | 9/2017 | Gilmore et al. |
| 2017/0304050 A1 | 10/2017 | Keidar et al. |
| 2017/0340433 A1 | 11/2017 | Berra et al. |
| 2017/0340443 A1 | 11/2017 | Stearns et al. |
| 2018/0185150 A1 | 7/2018 | Bishop et al. |
| 2018/0185151 A1 | 7/2018 | Bishop et al. |
| 2018/0185152 A1 | 7/2018 | Bishop et al. |
| 2018/0185153 A1 | 7/2018 | Bishop et al. |
| 2018/0206992 A1 | 7/2018 | Brown |
| 2018/0289480 A1 | 10/2018 | D'ambra et al. |
| 2018/0303614 A1 | 10/2018 | Schaffner et al. |
| 2018/0318079 A1 | 11/2018 | Patel et al. |
| 2018/0318083 A1 | 11/2018 | Bolling et al. |
| 2018/0360439 A1 | 12/2018 | Niland et al. |
| 2019/0000624 A1 | 1/2019 | Wilson et al. |
| 2019/0015205 A1 | 1/2019 | Rajagopal et al. |
| 2019/0151090 A1 | 5/2019 | Gross et al. |
| 2019/0175345 A1 | 6/2019 | Schaffner et al. |
| 2019/0175346 A1 | 6/2019 | Schaffner et al. |
| 2019/0183480 A1 | 6/2019 | Hiorth et al. |
| 2019/0216599 A1 | 7/2019 | Alkhatib |
| 2019/0216601 A1 | 7/2019 | Purcell et al. |
| 2019/0240023 A1 | 8/2019 | Spence et al. |
| 2019/0314155 A1 | 10/2019 | Franklin et al. |
| 2019/0328526 A1 | 10/2019 | Purcell et al. |
| 2019/0328528 A1 | 10/2019 | Purcell et al. |
| 2019/0328529 A1 | 10/2019 | Griswold et al. |
| 2019/0328530 A1 | 10/2019 | McDaniel et al. |
| 2019/0365539 A1 | 12/2019 | Rabito et al. |

FOREIGN PATENT DOCUMENTS

| | | |
|---|---|---|
| WO | WO 2008/005747 | 1/2008 |
| WO | WO 2010/128502 | 11/2010 |
| WO | WO 2012/040865 | 4/2012 |
| WO | WO 2017/066888 | 4/2017 |
| WO | WO 2017/066889 | 4/2017 |
| WO | WO 2017/066890 | 4/2017 |
| WO | WO 2017/117560 | 7/2017 |
| WO | WO 2018/126188 | 7/2018 |
| WO | WO 2019/177909 | 9/2019 |
| WO | WO 2019/231744 | 12/2019 |

OTHER PUBLICATIONS

Junior et al., "Surgical repair of chordae tendineae rupture after degenerative valvular regurgitation using stardardized bovine pericardium," (Jan. 2013) Rev Bras Cir Cardio, 28(1):36-46.
Kobayashi et al. "Ten Year Experience of Chordal Replacement with Expanded Polytetrafluoroethylene in Mitral Valve Repair," Circulation, AHA (Nov. 7, 2000) pp. III-30-III34.
Mar. 23, 2017 Int'l Search Report from Int'l App. No. PCT/US16/69567 (2 pgs).
Jun. 14, 2018 Int'l Search Report & Written Opinion from PCT/US17/069046 (10 pgs).
International Search Report and Written Opinion received in PCT Application No. PCT/US2019/021480, dated Jul. 15, 2019 in 16 pages.

* cited by examiner

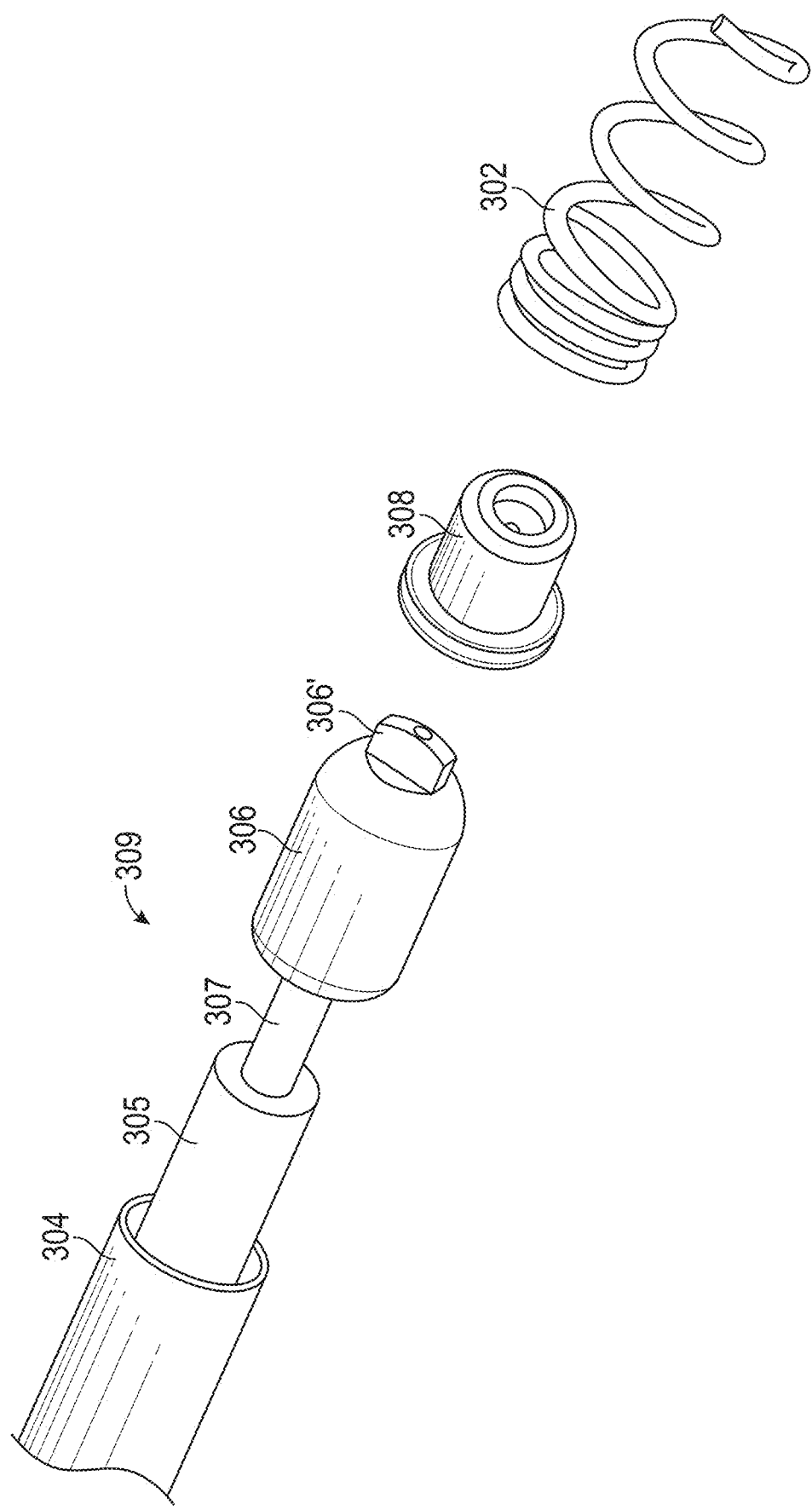

LEAFLET CAPTURE AND ANCHOR DEPLOYMENT SYSTEM

INCORPORATION BY REFERENCE TO ANY PRIORITY APPLICATIONS

This application is a continuation of U.S. application Ser. No. 16/297,422, filed Mar. 8, 2019, which claims the benefit under 35 U.S.C. § 119(e) of U.S. Provisional Application No. 62/641,612 filed Mar. 12, 2018, the entirety of which is hereby incorporated by reference herein for all purposes. U.S. application Ser. No. 16/297,422 also is a continuation-in-part of U.S. application Ser. No. 15/858,671, filed Dec. 29, 2017, which is a continuation-in-part of U.S. application Ser. No. 15/638,176, filed Jun. 29, 2017, now U.S. Pat. No. 9,877,833, which claims priority to U.S. Provisional Application 62/441,031, filed on Dec. 30, 2016, the entirety of each of these applications is hereby incorporated by reference herein for all purposes. Any and all applications for which a foreign or domestic priority claim is identified in the Application Data Sheet as filed with the present application are hereby incorporated by reference under 37 CFR 1.57.

BACKGROUND

The present disclosure relates to mitral valve repair or replacement and more generally to methods and methods and devices for mitral valve reshaping, repair and/or replacement of mitral chords to restore proper functioning of the mitral valve from a state of mitral valve regurgitation.

Description of the Related Art

The heart includes four heart valves, which allow blood to pass through the four chambers of the heart in one direction. The four valves are the tricuspid, mitral, pulmonary and aortic valves. The four chambers are the right and left atria (upper chambers) and right and left ventricle (lower chambers).

The mitral valve is formed by two leaflets, which are known as the anterior leaflet and the posterior leaflet, which open and close in response to pressure placed on the leaflets by the pumping of the heart. There are several problems that can develop or occur with respect to the mitral valve. Such problems include mitral valve regurgitation (MR), in which the mitral valve leaflets do not close properly, which can cause leakage of the mitral valve. Severe mitral regurgitation can adversely affect cardiac function and compromise a patient's quality of life and life-span.

Several techniques have been developed, for correcting mitral valve regurgitation. These include heart transplant, valve replacement or repair, chordae tendinea shortening or replacement and mitral annular repair also known as annuloplasty, depending upon the stage and underlying etiology.

As it relates to chordae tendinea replacement or repair, certain surgical and trans apical approaches have been proposed. Despite those efforts, however, there remains a need for a transvascular approach for chordae tendinea replacement or repair, to reduce or eliminate MR.

SUMMARY

An aspect of the invention includes a method of transvascular prosthetic chordae tendinae implantation, comprising the steps of: advancing a catheter into the left atrium, through the mitral valve, and into the left ventricle; deploying a ventricular anchor from the catheter and into a wall of the left ventricle, leaving a ventricular suture attached to the ventricular anchor and extending proximally through the catheter; from an atrium side, advancing a leaflet anchor through a superior surface of a mitral valve leaflet to position a leaflet anchor against the inferior (ventricular) side of the leaflet with a leaflet suture extending proximally through the leaflet, into and through the catheter; and securing the leaflet suture over the top of the leaflet coaptive edge to the ventricular suture to limit a range of travel of the leaflet in the direction of the left atrium.

Another aspect of the disclosure is a leaflet anchor deployment system, comprising: a catheter having a proximal end and a distal end; a leaflet anchor positioned on a distal end of the catheter; and a needle advanceable through the leaflet anchor, the needle releasably carrying a radially enlargeable leaflet anchor preloaded therein and having a suture extending proximally through the catheter.

In accordance with another aspect of the invention there is provided a method of transvascular prosthetic chordae tendinae implantation. The method comprises the steps of advancing a catheter into the left atrium, through the mitral valve, and into the left ventricle; deploying a ventricular anchor from the catheter and into a wall of the left ventricle, leaving a ventricular suture attached to the ventricular anchor and extending proximally through the catheter; from an atrium side, securing a leaflet anchor catheter to a mitral valve leaflet; with the leaflet anchor catheter secured to the leaflet, advancing a leaflet anchor from the catheter through the mitral valve leaflet to secure the mitral valve leaflet to a leaflet suture, with the leaflet suture extending proximally through the catheter; and securing the leaflet suture to the ventricular suture to limit a range of travel of the leaflet in the direction of the left atrium.

The step of advancing a leaflet anchor from the catheter through the mitral valve leaflet to secure the mitral valve leaflet to a leaflet suture may comprise advancing a needle preloaded with the leaflet anchor through the superior surface of the mitral valve leaflet. The securing a leaflet anchor catheter to a mitral valve leaflet step may comprise using a leaflet connector. The leaflet connector may comprise a helical anchor or a tissue hook.

In accordance with another aspect of the invention there is provided a method of securing a leaflet anchor to a mitral valve leaflet. The method comprises the steps of advancing a catheter into the left atrium; from an atrium side, securing a leaflet connector coupled to the catheter to a mitral valve leaflet from an atrial side of the leaflet; and after securing the leaflet connector to the mitral valve leaflet, advancing a leaflet anchor through the mitral valve leaflet to secure the mitral valve leaflet to a leaflet suture.

The step of advancing a leaflet anchor through the mitral valve leaflet to secure the mitral valve leaflet to a leaflet suture may comprise advancing a needle preloaded with the leaflet anchor through the mitral valve leaflet from the atrial side. The needle may be advanced through the leaflet connector. The leaflet connector may comprise a helical anchor.

In accordance with another aspect of the invention there is provided a leaflet anchor deployment system. The system comprises a catheter having a proximal end and a distal end; a leaflet connector positioned on a distal end of the catheter; and a needle advanceable through the leaflet connector, the needle including a radially enlargeable leaflet anchor preloaded therein and having a suture extending proximally through the catheter. The leaflet connector may comprise a helical anchor.

In accordance with another aspect of the invention there is provided a neo chordae tendinae deployment system. The system comprises a catheter having a proximal end and a distal end; a helical ventricular anchor subassembly extendable through the catheter, having a ventricular suture extending proximally through the catheter; and a leaflet anchor deployment subassembly extendable through the catheter, having a radially enlargeable leaflet anchor within the subassembly and having a leaflet suture extending proximally through the catheter.

The radially enlargeable leaflet anchor may comprise a pledget. The pledget may be transformable from an elongate strip configuration to a radially enlarged, axially shortened configuration by proximal retraction of the suture. The radially enlargeable leaflet anchor may comprise the leaflet suture positioned between two sheets of material. The radially enlargeable leaflet anchor may be carried within a needle having a sharpened end for piercing the leaflet. The leaflet anchor deployment subassembly may comprise an elongate tube having a distal end and a central lumen, and a leaflet connector on the distal end. The leaflet connector may comprise a helical leaflet anchor. The needle may be axially movable with respect to the helical leaflet anchor. The system may further comprise a suture locking subassembly, advanceable through the catheter and configured to connect the ventricular suture to the leaflet suture.

In accordance with another aspect of the invention there is provided a leaflet anchor delivery subsystem. The subsystem comprises an elongate flexible tubular body, having a proximal end, a distal end and a central lumen; a deployment needle axially movably advancable through the central lumen; a leaflet anchor carried within the deployment needle; and a leaflet connector carried by the distal end of the tubular body. The leaflet anchor may comprise a helical element. The deployment needle may be axially extendable through the helical element.

In accordance with another aspect of the invention there is provided a tissue anchor. The tissue anchor comprises a hub; a suture extending proximally from the hub; a helical anchor extending distally from the hub; a core wire extending concentrically through the helical anchor, and beyond the distal end of the helical anchor.

The tissue anchor may further comprise a suture anchor guide extending proximally from the hub. The tissue anchor may further comprise a tubular sleeve having a length of no more than about 10 cm extending proximally from the hub. The tissue anchor may further comprise a radiopaque marker carried by the sleeve. The tissue anchor may further comprise a radiopaque marker axially movably carried by the core wire. The tissue anchor may further comprise a spring carried by the core wire. The tissue anchor may further comprise a tissue piercing point on a distal end of the helical anchor, and a barb on the helical anchor configured to resist rotation of the helical anchor out of engagement with tissue.

In accordance with another aspect of the invention there is provided a tissue anchor with dynamic depth indicator. The tissue anchor comprises a hub; a tissue anchor extending distally from the hub; a core wire extending distally from the hub; a radiopaque marker movably carried by the hub; and a spring for biasing the radiopaque marker in a distal direction; wherein the radiopaque marker is advanced proximally with respect to the tissue anchor in response to the tissue anchor advancing into tissue.

In accordance with another aspect of the invention there is provided an endovascular suture lock. The suture lock comprises a body having a suture path extending therethrough; a movable wall in the housing, for reducing a cross sectional dimension of the suture path; a rotatable coupling on the housing; and a drive mechanism for advancing the movable wall in response to rotation of the coupling.

The suture lock may additionally comprise a friction enhancing surface exposed to the suture path. The friction enhancing surface may be on the movable wall. The suture lock may comprise a push wedge having an angled surface and axially movable within the housing. Rotation of the coupling may advance the push wedge axially which advances the movable wall laterally to change the cross sectional dimension of the suture path. The movable wall may comprise a suture gripping surface on a first side and a ramp surface on a second side, the ramp surface configured for sliding contact with the angled surface on the push wedge.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting on scope.

FIG. 2E is a partially exploded perspective view of a ventricular anchor and the distal end of a ventricular anchor deployment tool.

DETAILED DESCRIPTION OF THE PREFERRED EMBODIMENTS

U.S. patent application Ser. No. 15/858,671, filed Dec. 29, 2017 (the entirety of which is hereby incorporated by reference herein discloses systems and methods for the transvascular prosthetic chordae tendinae implantation. One aspect involves advancing a catheter into the left atrium, through the mitral valve, and into the left ventricle; deploying a ventricular anchor from the catheter and into a wall of the left ventricle, leaving a ventricular suture attached to the ventricular anchor and extending proximally through the catheter; and advancing a leaflet anchor into a mitral valve leaflet to secure the mitral valve leaflet to a leaflet suture, with the leaflet suture extending proximally through the catheter, and extending the leaflet suture over the top of the coaptive edge and securing the leaflet suture to the ventricular suture to limit a range of travel of the leaflet in the direction of the left atrium. Certain aspects are developed further herein.

The approach to the mitral valve can be accomplished through a standard transceptal approach to provide access to the left atrium. With this access, a first step can include securing a leaflet capture catheter to the leaflet of the mitral valve in the location determined to best correct regurgitation. Probing the surface of the leaflet from the superior atrium surface can advantageously provide immediate feedback as to the optimal location to add an additional mitral valve chord. In another implementation of the invention, the ventricular anchor is deployed first, followed by deployment of the leaflet anchor.

Figure 1:
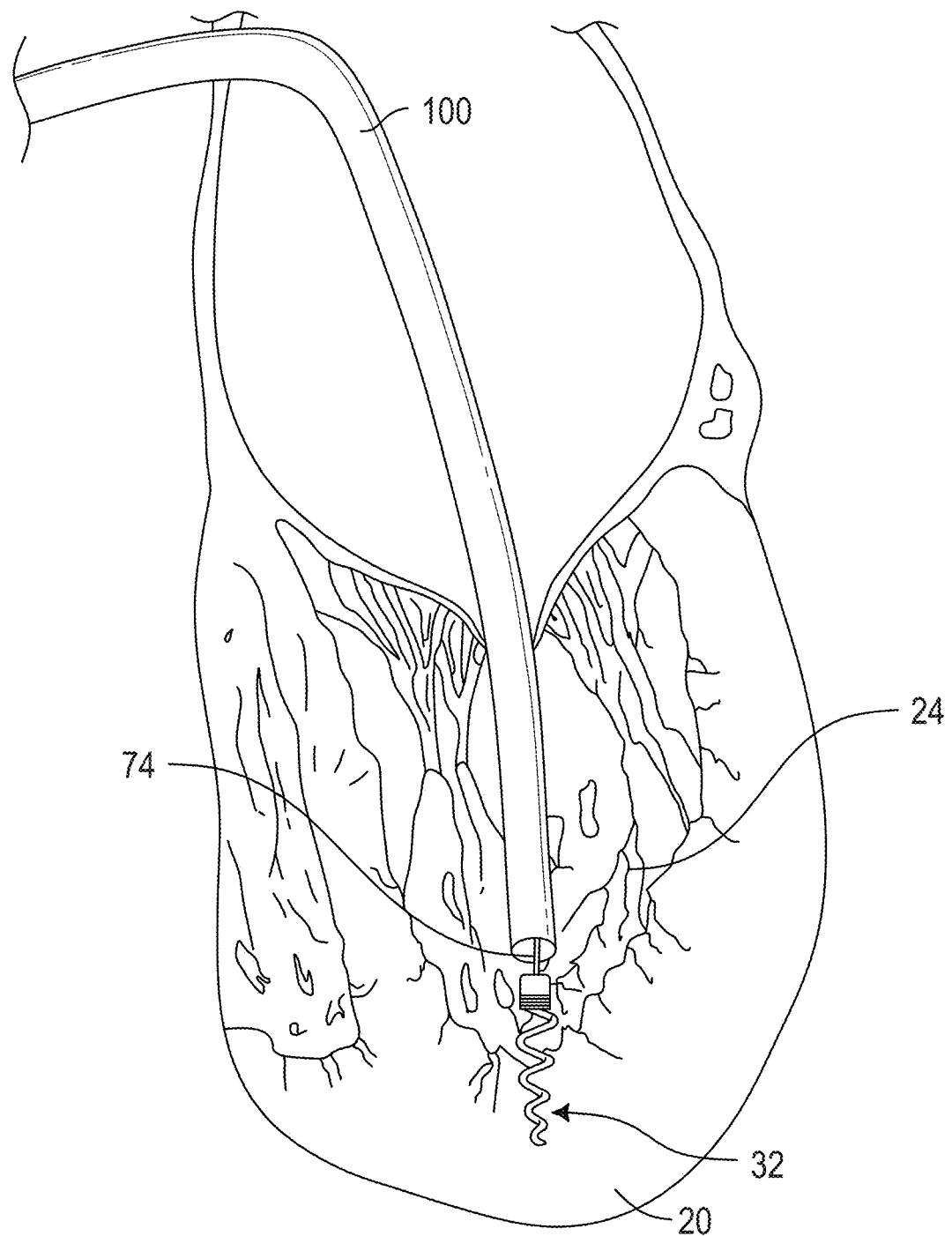
FIG. 1 illustrates placement of a ventricular anchor via transceptal approach to the mitral valve.

Referring to FIG. 1, a ventricular anchor such as a helical anchor 32 has been deployed near the apex 20 of the left ventricle 24. While the helical anchor 32 is shown positioned near the apex 20 in the following Figures, the anchor 32 can be attached at a point that is offset from the thin tissue of the apex, and can be instead implanted in the generally thicker adjacent wall of the ventricle, such as between the two papillary muscles. This allows the implanted neo chord construct (suture, optional neo papillary muscle, and/or the helical anchor) to be aligned along a longitudinal axis substantially parallel to or concentric with the original path of the native chord. In certain embodiments, the implanted neo chord construct is aligned along a longitudinal axis that is within 5 degrees, 10 degrees, or 15 degrees of being parallel with the original path of the native chord and/or the path of the adjacent native chord. In addition, while a helical anchor is illustrated the anchor can have a different structure for engaging tissue of the heart and thus other tissue anchor structures can be used instead of a helical structure including various piercing, hook or radially expandable structures known for engaging tissue.

Figure 2A:
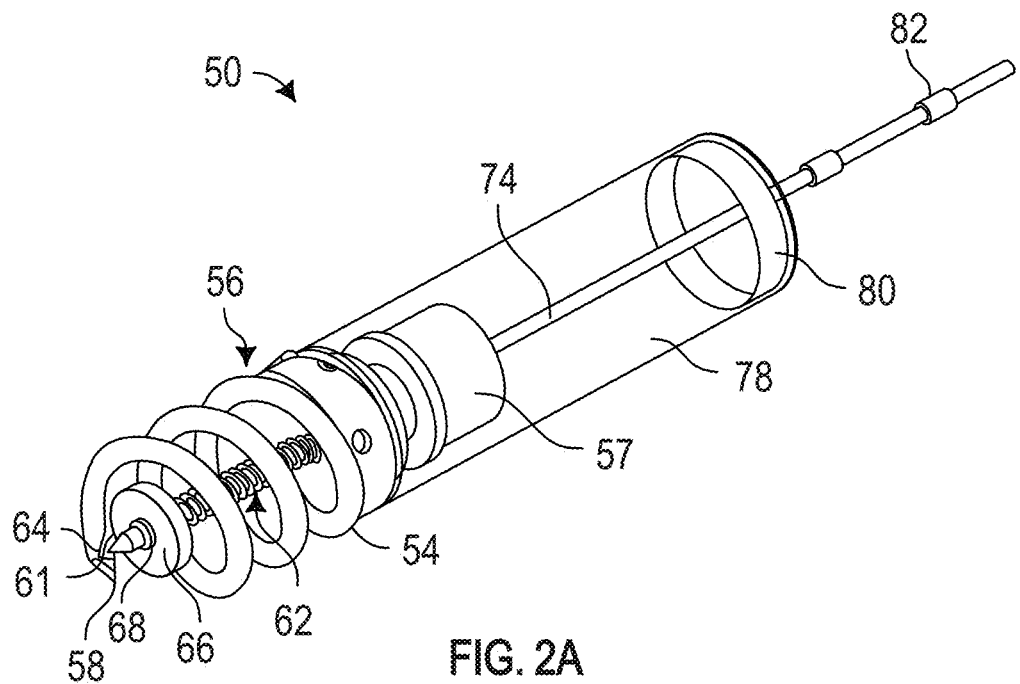
FIGS. 2A and 2B illustrate a ventricular anchor.
Figure 2B:
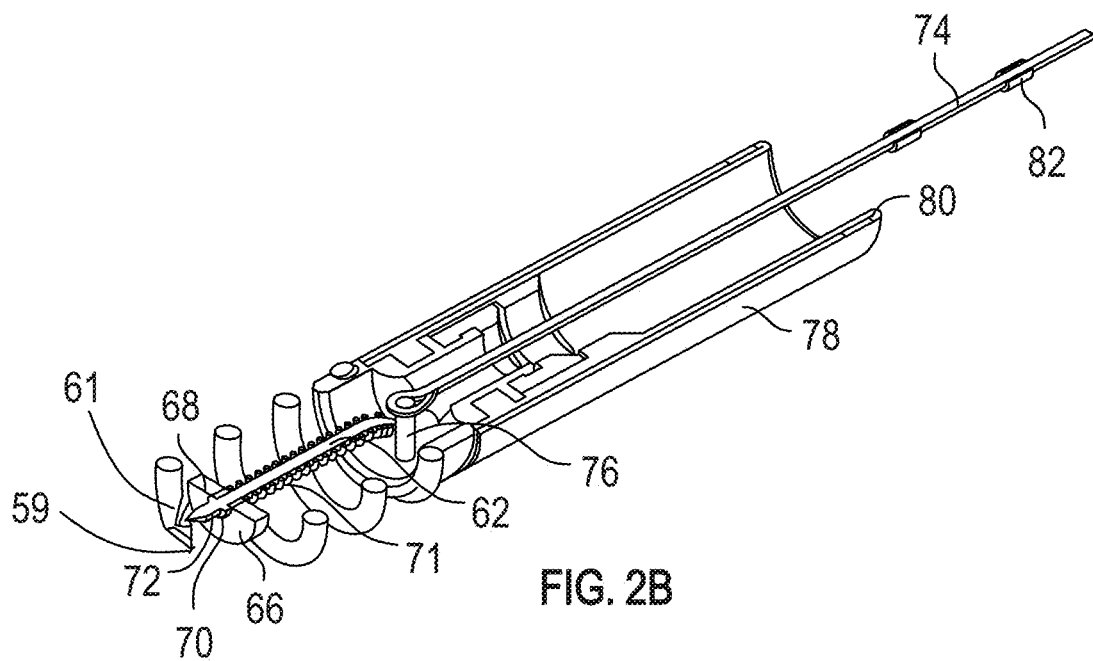

Referring to FIGS. 2A and 2B, there is illustrated one implementation of a tissue anchor suitable for use as a ventricular anchor in accordance with the present invention. The anchor assembly 50 will be described primarily in the context of the present chordae repair application, however the anchor may be utilized in any of a wide variety of other applications where a soft tissue or bone anchor may be desired.

The anchor assembly 50 generally comprises a coil 54 which may comprise any of a variety of materials such as stainless steel or Nitinol. The coil 54 extends helically between a proximal end 56 and a distal end 58. Distal end 58 is provided with a sharpened tip 59, and also carries a retention barb 61, configured to resist reverse rotation of the coil and detachment from tissue. The proximal end 56 of the coil 54 is carried by (attached to or formed integrally with) a hub 57 discussed in additional detail below.

Extending distally from the hub 57 and within the coil 54 is an elongate core wire 62 having a sharp, tissue piercing distal end 64. The distal end 64 is positioned distally of the distal end 58 of the coil 54. This enables the sharp distal end 64 to pierce tissue upon contact, and prior to beginning rotation of the coil 54 to embed the coil 54 within the target tissue. Engaging the tip 64 prior to rotation of the anchor stabilizes the anchor against sideways movement allowing a single placement of the anchor 50 against tissue, and rotation of the coil 54 to engage tissue, without 'walking' of the anchor away from the desired target site as will be understood by those of skill in the art. A proximal end of the core wire 62 may be attached to the hub in any of a variety of ways, such as by soldering, brazing, adhesives and/or mechanical interference such as by entering an aperture in a sidewall or other surface of the hub 57.

A radiopaque depth marker 66 is provided with an aperture 68 and is axially movably carried on the core wire 62. A distal stop 70 such as a radially outwardly extending protrusion or annular ridge is carried by the core wire 62, and spaced proximally of the sharpened distal end 64 to provide a core wire leading segment 72 on the distal side of the stop 70 so that the marker 66 cannot interfere with the tissue anchoring function of the distal tip 64. The stop 70 functions to limit distal travel of the marker 66. The marker 66 may be an annular structure such as a circular disc with a central aperture to receive the core wire 62.

A coil spring 71 is concentrically carried over the core wire 62 and biases the radiopaque marker 66 in the distal direction. The radiopaque marker 66 is thus held in position against a proximal surface of the stop 70. In use, the marker 66 rides on the surface of tissue at the target attachment site. As the helical coil anchor 54 is rotated and advances distally into tissue, the marker 66 rides proximally on the core wire 62 along with the tissue surface, compressing the coil spring 71 until the marker 66 is retracted proximally to the hub when the tissue anchor is fully embedded. This enables fluoroscopic visualization of the progress of the coil into tissue and of the fully engaged end point of embedding the coil 54 into the target tissue, by observing the changing distance between marker 66 and a reference such as the hub 57 or other radiopaque marker.

The hub 57 comprises a proximal connector for engagement with a rotational driver as discussed elsewhere herein. In one implementation, the connector comprises an aperture such as a hexagonal aperture for removably engaging a complementary surface structure on the distal end of the driver. A suture 74 is secured to the anchor assembly 50, for example secured to the hub 57, coil 54 or core wire 62. In the illustrated embodiment, the suture 74 is attached to a cross pin 76 which may be inserted through one or two apertures in the sidewall of the hub and across a central hub lumen. The suture may additionally carry one or two more radiopaque markers 82 spaced apart from the hub 57, and may extend proximally through the proximal connector and a central lumen in the rotational driver.

A suture lock guide such as a tubular sleeve 78 extends proximally from the hub 57 for at least about 2 mm or 4 mm or 8 mm but generally no more than about 5 cm or 2 cm depending upon desired performance. The guide sleeve 78 may comprise a flexible material such as ePTFE. Preferably a radiopaque marker band 80 is carried by the proximal end of sleeve 78 and spaced axially apart from the marker 82 on suture 74, to facilitate fluoroscopic visualization of the suture lock as it is advanced distally over the suture 74. The marker band 80 may be positioned in between an inner layer and an outer layer of ePTFE sleeve, such as may result from placing the band over the sleeve and inverting the sleeve over itself to entrap the ring.

The suture lock guide may comprise any of a variety of structures such as a sleeve as illustrated or an alignment pin extending proximally from the hub and received within a lumen in the suture lock, for maintaining the orientation of the suture lock following detachment from the deployment catheter. Since the tension on the suture is optimized while the suture lock is held in place by the deployment catheter, any change in the orientation of the suture lock following release from the catheter would affect tension on the leaflet and potentially negatively affect the therapeutic value of the implant. The suture lock guide helps maintain constant the maximum distance between the ventricular anchor and the leaflet anchor both pre and post deployment from the catheter. In this manner the maximum tension on the leaflet suture (during systole) remains unchanged after the suture lock has been locked, both before and after detachment of the catheter.

Figure 2C:
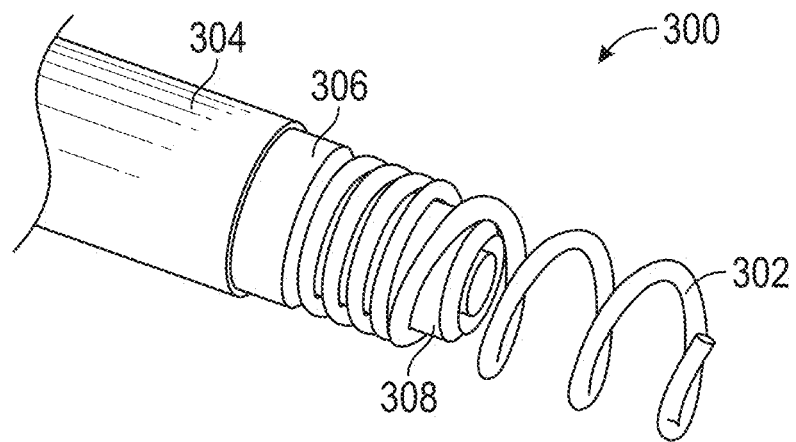
FIG. 2C is a perspective view of a ventricular anchor on the distal end of a ventricular anchor deployment tool.
Figure 2D:
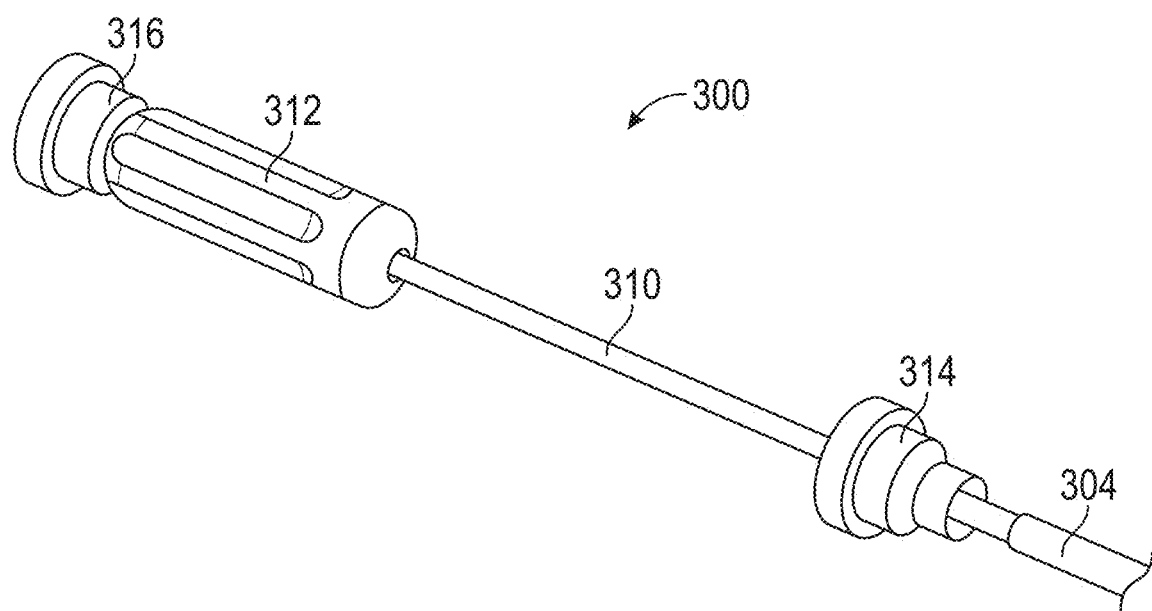
FIG. 2D is a perspective view of the proximal end of a ventricular anchor deployment tool.

The helical anchor assembly 50 may be delivered by a ventricular anchor delivery subsystem 300. FIGS. 2C-2E illustrate various views of a ventricular anchor delivery subsystem 300 and its components. FIG. 2C depicts a perspective view of a distal end of the subsystem 300. FIG. 2D depicts a perspective view of a proximal end of the subsystem 300. FIG. 2E depicts a partially exploded view of a distal end of the subsystem 300.

The subsystem 300 may be delivered through the delivery catheter 100. The delivery catheter 100 may access the left atrium through conventional techniques, such as through an atrial trans-septal puncture. The delivery catheter 100 may be maintained in a substantially constant location throughout the procedure as various subsystems are placed and removed from the delivery catheter 100. For instance, the distal end of the delivery catheter 100 may be positioned in the left atrium. In other implementations, the distal end of the delivery catheter 100 may be positioned in the left ventricle throughout the duration of the procedure.

As shown in FIGS. 2C-2E, the ventricular anchor delivery subsystem 300 may comprise an outer sheath 304, a driver (comprising shaft 307 and head 306), an anchor hub 308, and an anchor 302. The anchor may be a helical anchor 302 and the drive head 306 can be configured to rotate the helical anchor 302. The helical anchor 302 may comprise an inner diameter configured to be received over the outer diameter of an anchor hub 308. The helical anchor 302 may be securely fixed secured to the anchor hub 308 by an interference fit or other frictional engagement, soldering or other known attachment technique. The anchor hub 308 may be left implanted along with the helical anchor 302.

The anchor hub 308 may comprise a lumen positioned substantially along a central axis of the anchor hub 308 for receiving a suture 74 (FIG. 2A) and attaching the suture 74 to the helical anchor 302. In some embodiments, the suture 74 may comprise an attachment element (e.g. a knot or a washer) with a diameter sized to prevent the suture 74 from being pulled proximally through the anchor hub 308 lumen. For example, the suture 74 may be knotted on a distal side of the lumen. In some embodiments, the suture 74 may be tied to the anchor hub 308 (e.g., passed through the lumen, wrapped around a structure such as the outer surface or a cross pin 76 as shown in FIG. 2B, and tied to itself).

The helical anchor 302 may comprise a distal section of windings and a proximal section of windings. The proximal section of windings may be spaced closer together than the distal section of windings and may be configured for securing the helical anchor 302 to the anchor hub 308. The distal section of windings may be spaced further apart than the proximal section of windings and may be configured for insertion into the ventricular tissue. The anchor hub 308 may comprise an enlarged cross-section at its proximal end configured to abut the helical anchor 302 and/or prevent the helical anchor 302 from advancing proximally over the proximal end of the anchor hub 308. Other helical anchors, such as those described elsewhere herein, may be configured to be used with the ventricular anchor delivery subsystem 300 described herein as well.

The proximal face of the helical anchor 308 may comprise a recess for receiving an extending portion 306' of the driver head 306. The recess may be non-circular (e.g., oblong or polygonal such as hexagonal) such that it is configured to transfer torque from the driver to the anchor hub 308 upon rotation of the driver. The recess may be positioned around the central lumen of the anchor hub 308.

In other embodiments, the anchor hub 308 may comprise an extending portion and the driver 306 may have a complementary recess. The driver head 306 may be generally cylindrical, with a distally facing post or aperture with a complementary configuration to rotationally engage the corresponding component on the anchor. The driver head 306 may be fixedly coupled to a drive shaft 307. The driver may comprise a central lumen through the driver head 306 and drive shaft 307 configured to receive the suture 74. The central lumen of the driver may be configured to be aligned with the central lumen of the anchor hub 308. The drive shaft 307 may be received within a guide shaft 305. The diameter of the driver head 306 may be larger than the inner diameter of the guide shaft 305. The outer sheath 304 may be sized to receive the guide shaft 305 as well as the driver head 306, the anchor hub 308, and the helical anchor 302.

The outer sheath 304 may be delivered into the left ventricle and proximal to the ventricular attachment site via the delivery catheter 100. In some embodiments, the outer sheath 304 may be delivered without a delivery catheter. In some implementations, the helical anchor 302 may be concealed within the outer sheath 304 until the outer sheath 304 is positioned proximal to the ventricular attachment site then pushed distally through the outer sheath 304 or the outer sheath 304 is proximally retracted so that the helical anchor 302 is exposed. The helical anchor 302 may be placed into contact with the ventricular tissue. Rotation of the drive shaft 307 may cause the driver head 306, the anchor hub 308, and the helical anchor 302 to rotate thereby screwing the ventricular anchor 302 into the ventricular tissue. Rotation of the driver 309 may axially advance the driver 309, anchor hub 308, and helical screw 302 in a distal direction with respect to the outer sheath 304.

The drive shaft 307 may be rotated manually by a user using a drive handle 312, as shown in FIG. 2D. The proximal end of the ventricular anchor delivery subsystem 300, as illustrated in FIG. 2D, may comprise first and second hemostasis valves 314, 316. The first hemostasis valve 314 may be positioned distal to the drive handle 312 and may provide access to the guide shaft 305. The second hemostasis valve 316 may be positioned proximal to the drive handle 312 and may provide access to the central lumen of the driver. The ventricular anchor suture (not shown) may extend through the second hemostasis valve 316.

In some implementations, the inserting portion 306' of the driver head 306 and the recess of the anchor hub 308 may have a frictional engagement that transiently holds the two components together. The frictional engagement may be overcome upon proximal retraction of the driver by a counter force from the ventricular tissue once the helical anchor 302 is inserted. In some implementations, proximal tension on the suture 74 may provide an engagement force between the proximal hub 308 and the driver head 306, which can be released upon retraction of the driver 309. The driver head 306 may be proximally withdrawn into the outer sheath 304 before the outer sheath 304 is withdrawn into the delivery catheter 100.

The non-implanted components of the ventricular anchor delivery subsystem 300 may be removed from the delivery catheter 100 and subsequent subsystems may be placed in the delivery catheter 100 for completing implantation of the neo chordae. In a modified embodiment, the ventricular anchor delivery subsystem 300 and subsequent subsystems such as the leaflet anchor delivery subsystem 330 may be positioned within the delivery catheter 100 at the same time and in certain arrangements the tissue and leaflet anchors can both be preloaded into the delivery catheter. In alternative embodiments, the implantation of the ventricular anchor may be performed in a different order (e.g., after the implantation of the leaflet anchor). The ventricular anchor delivery components may be proximally retracted over a proximal end of the suture 74, which may remain extending through the delivery catheter 100 to the ventricular anchor 302.

Figure 3:
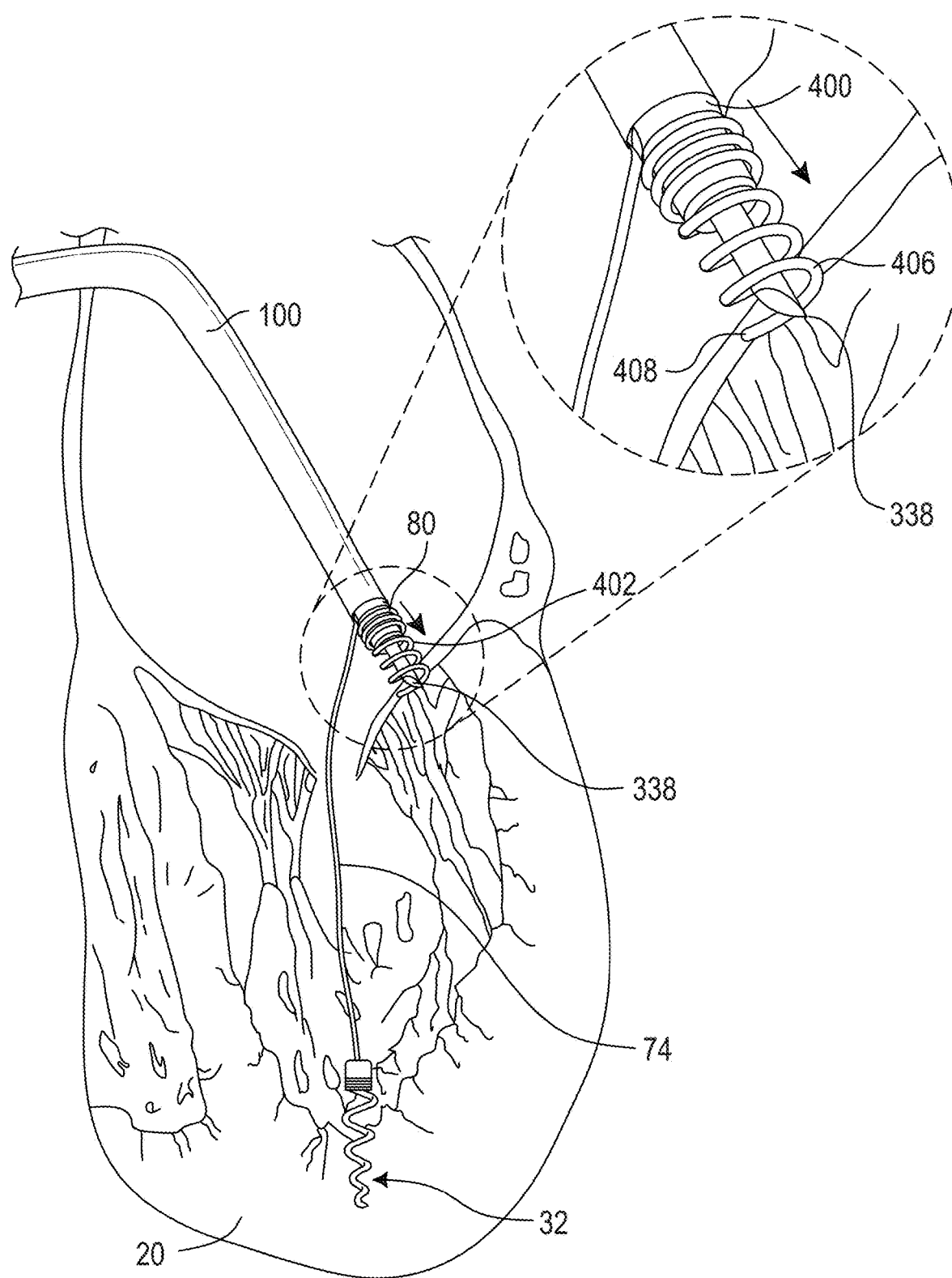
FIG. 3 illustrates the deployment end of a catheter positioned to engage a leaflet of the mitral valve.

FIGS. 3-6 depict the deployment of the leaflet anchor. Referring to FIG. 3, the ventricular anchor 32 has been deployed and is tethered to the catheter 100 by a ventricular anchor suture 74 and the ventricular anchor subsystem has been removed. The leaflet anchor is carried within a needle 338, shown aimed at a target site on the atrial side of the leaflet. The needle 338 is axially reciprocally carried within the catheter 100, such as within a tubular sleeve 332 advanceable through the catheter 100. Additional details of the needle and needle driver are discussed below.

Figure 4:
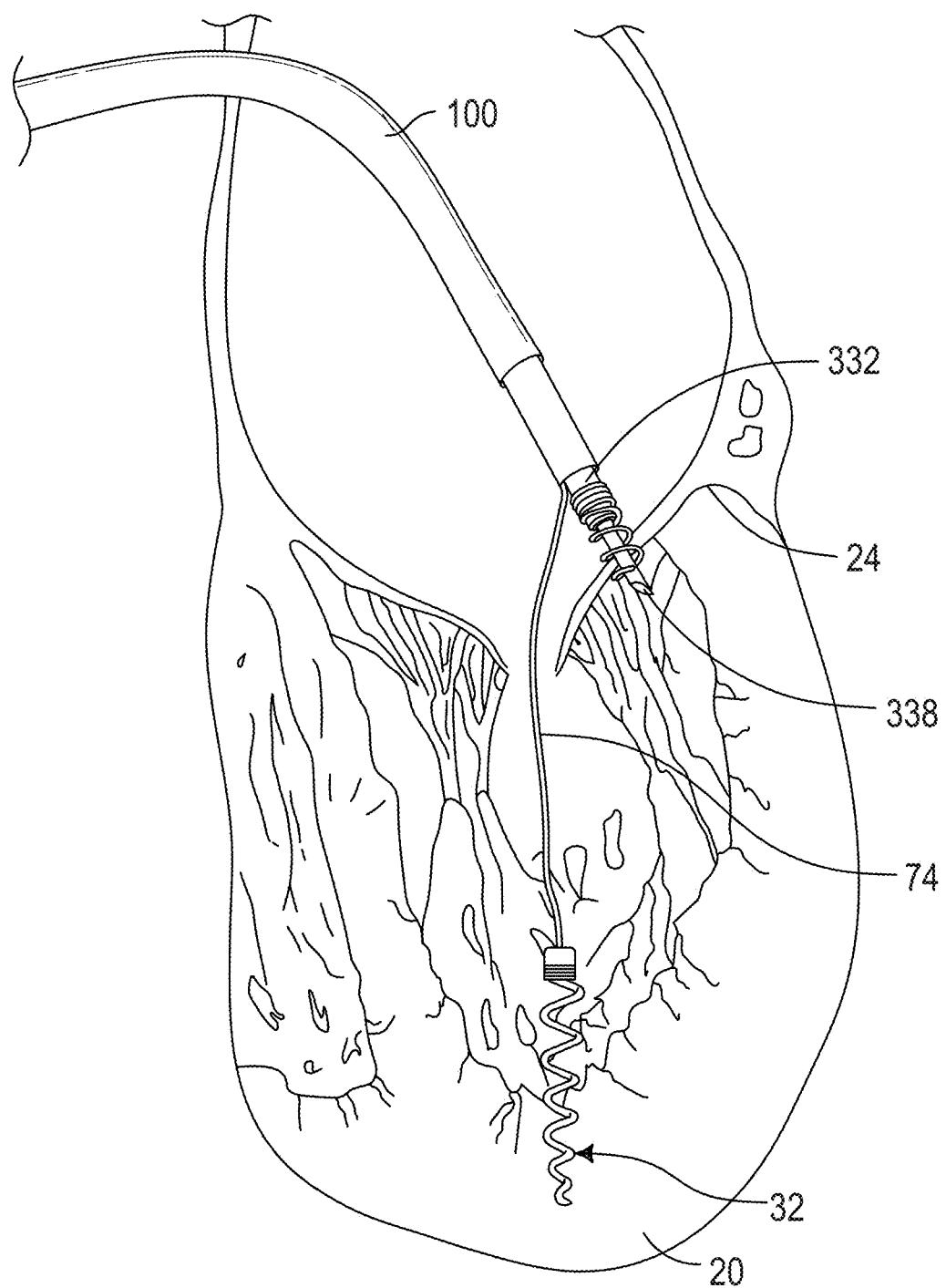
FIG. 4 illustrates the leaflet captured by the helical leaflet anchor, and a needle crossing through the leaflet from the atrium to the ventricle.

As shown in FIG. 3, in the illustrated arrangement, the needle can cross through the leaflet from the atrium to the ventricle and a preloaded suture can then be advanced into the ventricle. The suture can then be used to collapse the pledget against the ventricular side of the leaflet to anchor the suture to the leaflet as shown in FIG. 4. Thus the pledget forms a radially enlargeable leaflet anchor. In certain embodiments, other forms of a radially enlargeable leaflet anchor can be used.

Figure 5:
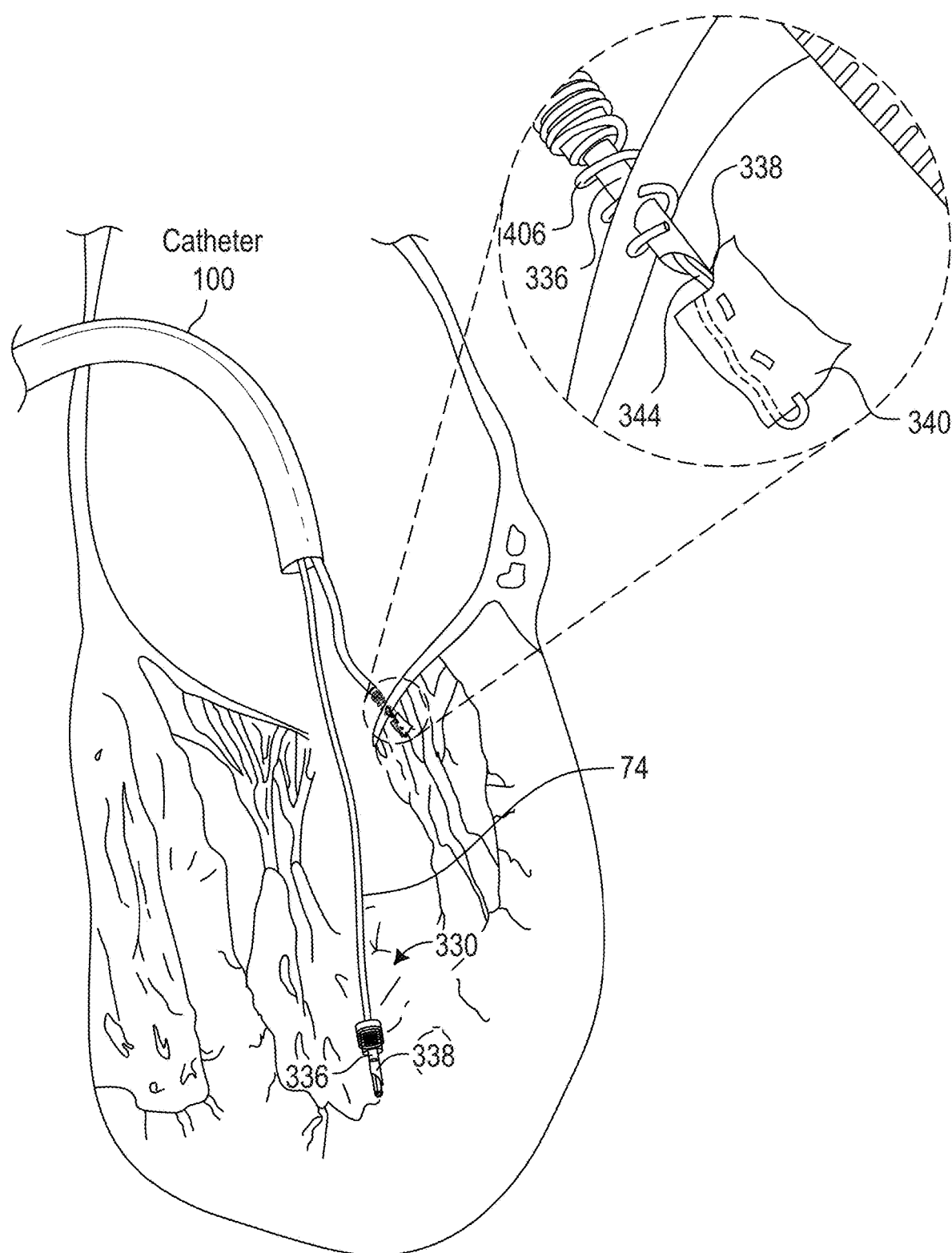
FIG. 5 illustrates a pledget type leaflet anchor deployed from the needle and into the ventricle.

The leaflet anchor and suture can then be used in combination with a ventricular anchor, suture and suture lock to effectively create a new mitral chord as shown in FIG. 5. As noted above, the leaflet anchor and suture can be used in combination with the systems and methods for the transvascular prosthetic chordae tendinae implantation disclosed in the U.S. patent application Ser. No. 15/858,671 (the entirety of which is incorporated by reference herein) and the various embodiments of ventricular anchors, sutures and suture locks disclosed therein.

Preferably, the leaflet anchor deployment subassembly is provided with a temporary anchor for capturing and stabilizing the leaflet while the needle tip 338 is advanced therethrough at a target side. As illustrated in FIG. 3 and FIG. 4, a distal end 400 of delivery tube 332 or other system component carries a temporary tissue anchor such as a helical tissue anchor 402. Anchor 402 may be similar to ventricular anchor 54 except that temporary anchor 402 does not have a distal barb since it is intended to be only momentarily in engagement with the leaflet. The anchor 402 thus comprises a helical element 406 which terminates in a distal tip 408.

In use, the distal tip 408 is positioned at a target site on the surface of the leaflet, and the helical element 406 is rotated about its axis to engage and penetrate the leaflet. The needle tip 338 may be optionally engaged with the leaflet prior to rotation of the helical element 406, and utilized to stabilize the anchor against moving away from the target site in response to rotation, in a manner similar to that discussed in connection with the ventricular anchor and FIGS. 2A and 2B.

Following engagement of the helical element 406 to capture the leaflet from the atrial side and secure the leaflet to the catheter, the needle may be advanced distally through the central lumen defined by the helical element 406 and completely through the leaflet so that the needle tip 338 exits the ventricular side of the leaflet as seen in FIG. 4. An anchor deployment actuator such as a pusher extending through the needle may be utilized to deploy the anchor from the needle and into the ventricle.

Figure 7:
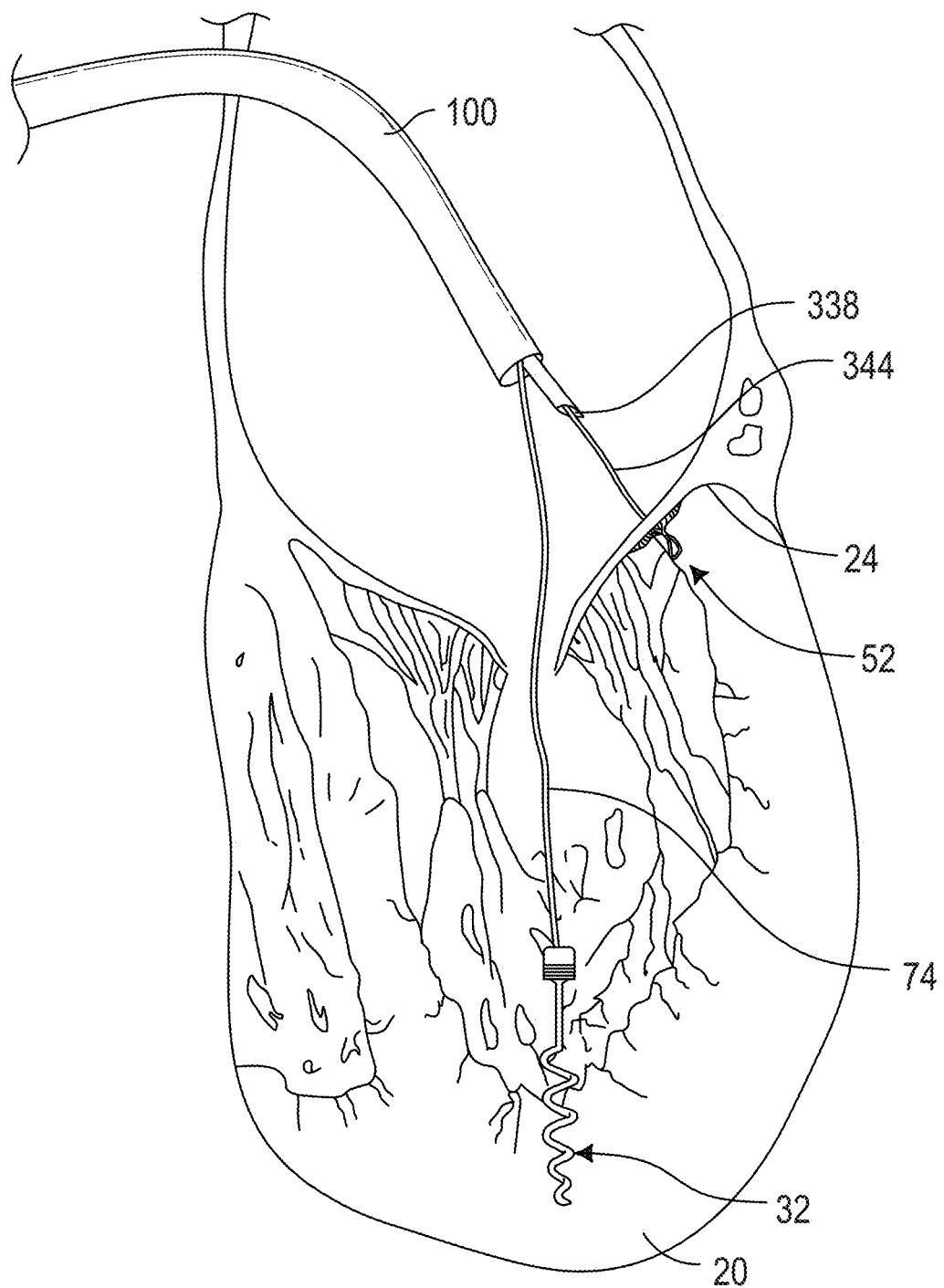
FIG. 7 illustrates a deployed leaflet anchor and suture and a deployed ventricular anchor and suture ready for tensioning and attachment of a suture lock.
Figure 8:
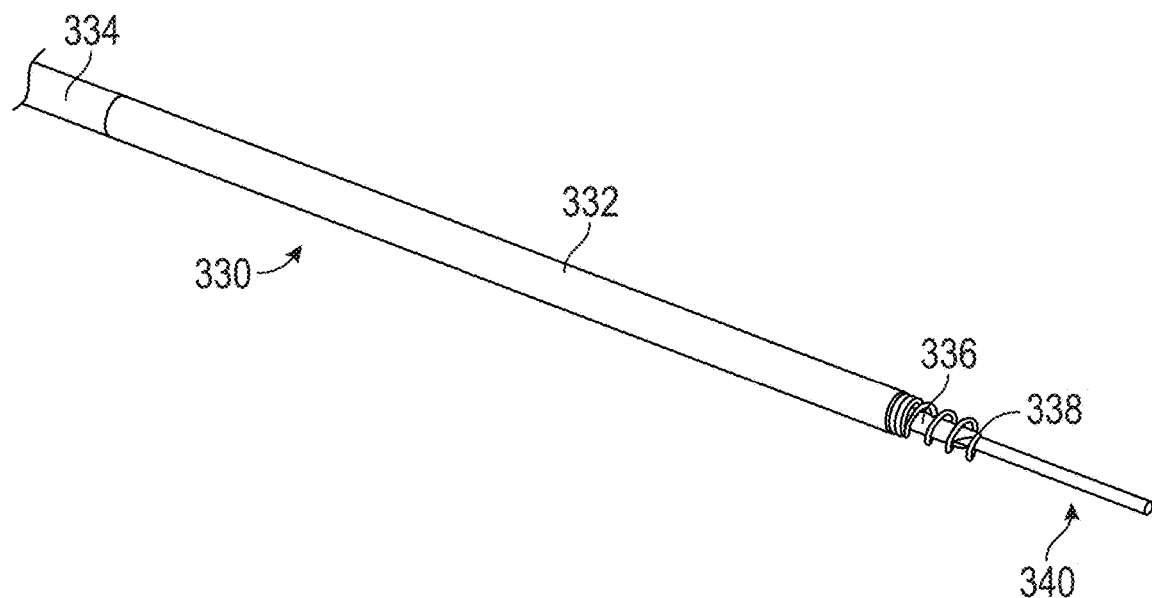
FIG. 8 illustrates a perspective view of a distal end of the leaflet anchor delivery subsystem.
Figure 10:
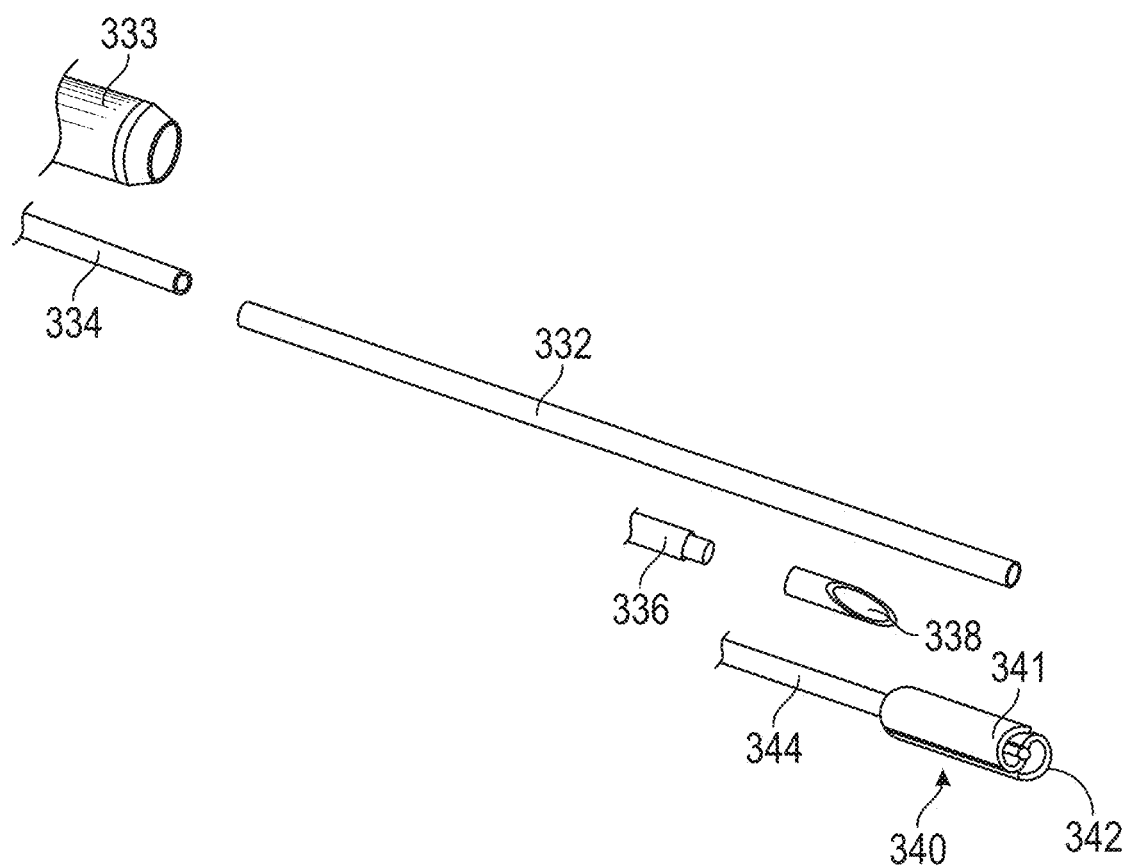
FIG. 10 illustrates an exploded view of the distal end of the leaflet anchor delivery subsystem.

Referring to FIG. 5, the leaflet anchor may be a pledget 340 similar to those described elsewhere herein. The pledget 340 may be coupled or attached to the distal end of a leaflet anchor suture 344. The pledget may comprise a soft and/or flexible material such as a fabric. The suture 344 may extend through the needle 336. The pledget 340 may be folded or compressed in a conformation comprising a reduced radial cross section such that it may be disposed within the needle 336 for delivery, as shown in FIGS. 8 and 10 discussed below. The pledget 340 may expand from a reduced cross section to assume a larger radial cross section upon deployment from the distal end of the needle tip 338, as shown in FIG. 5. In some embodiments, the pledget 340 may be pushed through the needle 336 via a push wire or release wire (not shown). Upon delivery through the needle tip 338, proximal retraction of the leaflet suture 344 as shown in FIG. 6 may cause the leaflet anchor to assume an axially collapsed, radially enlarged conformation which prevents the leaflet anchor from being retracted through the puncture in the leaflet and thereby anchors the leaflet suture 344 to the leaflet, as shown in FIG. 7.

Figure 6A:
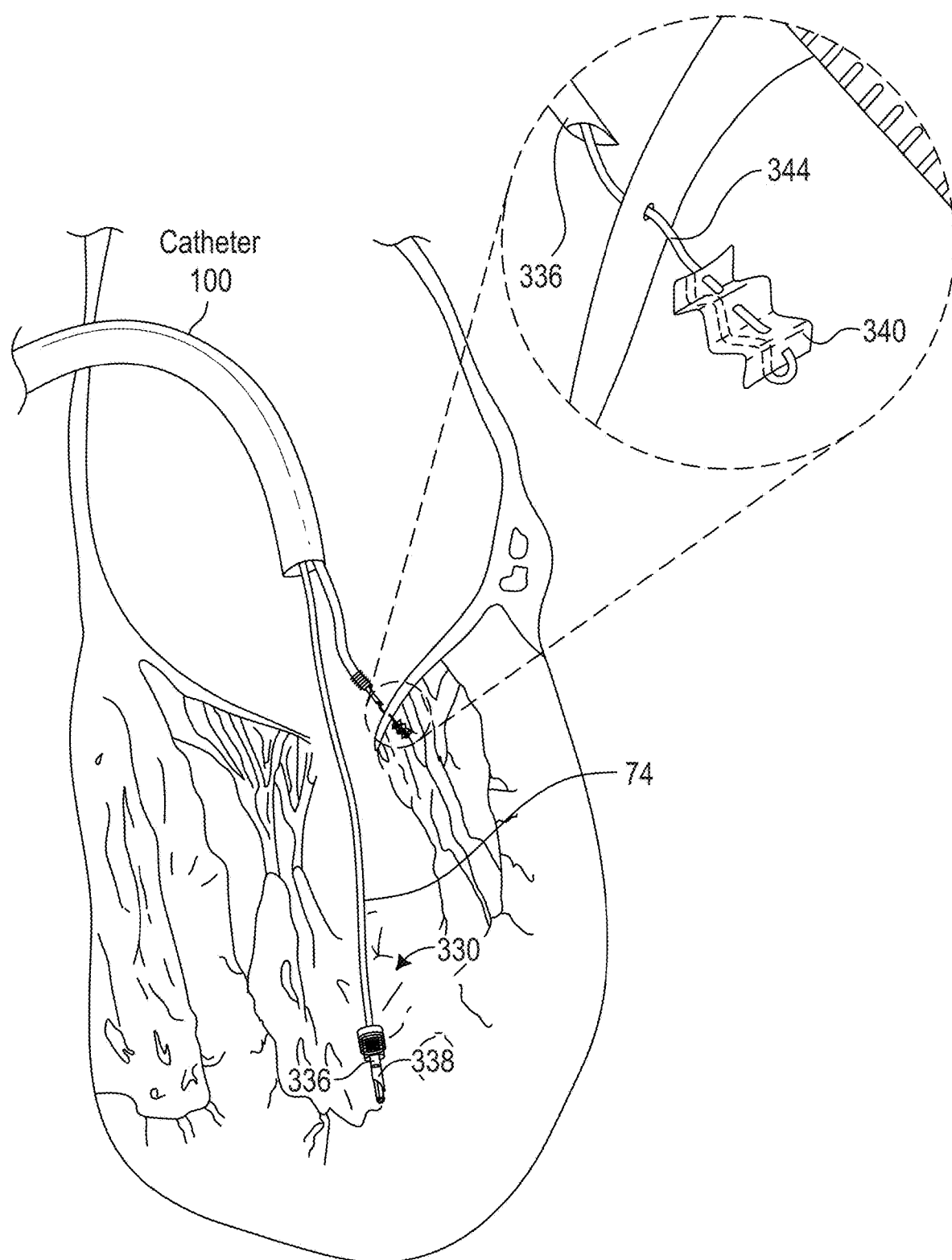
FIG. 6A illustrates proximal traction on a leaflet suture to collapse the pledget against the ventricular side of the leaflet.

FIGS. 6A-6D schematically depict a pledget 340 connected to the distal end of a leaflet suture 344. The pledget 340 may comprise two wings 341, 342, which may be rolled/folded (e.g., both in a clockwise or counterclockwise direction) around a longitudinal axis of the pledget 340 to form a reduced cross section conformation. In some embodiments, the leaflet suture 344 may be integrally formed with the pledget 340. In order to produce a foldable or collapsible configuration, the suture 344 may extend distally through the pledget, loop around the distal end of the pledget and return proximally and threaded back through one or more apertures (e.g., two apertures, three apertures, four apertures, etc.) formed in the pledget 340, as shown in FIG. 6A. In some embodiments, the apertures may be aligned along a center of the pledget 340.

The apertures may extend through the pledget 340 and through the portion of the embedded portion of the suture 344 which is integral with the pledget 340. The embedded portion of the suture 344 may be at least partially flatted within the pledget 340. In some embodiments, the apertures may be placed substantially near the center of the pledget (e.g., immediately to the left or right of the embedded suture 344 or alternating between the left and right side of the suture 344). When deployed the suture 344 may be effectively joined to a distal end of the pledget 340 (e.g., the suture 344 may loop back to where it inserts between the pledget sheets).

Figure 6B:
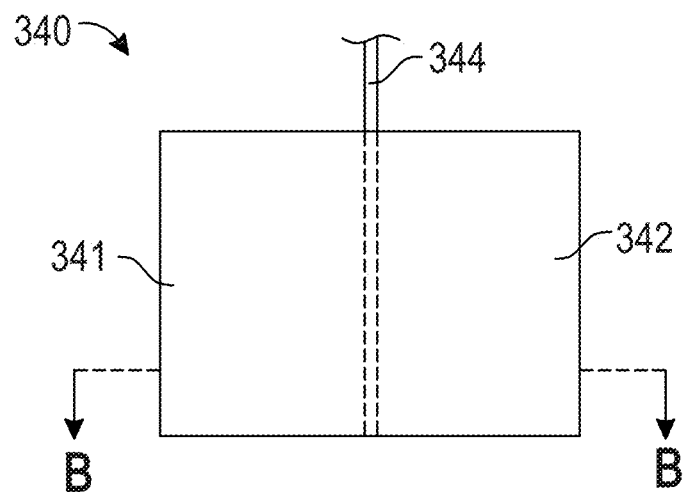
FIGS. 6B-6D illustrate details of a pledget type leaflet anchor.
Figure 6C:
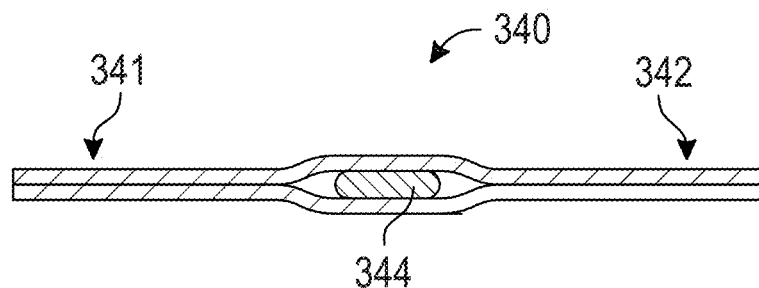
Figure 6D:
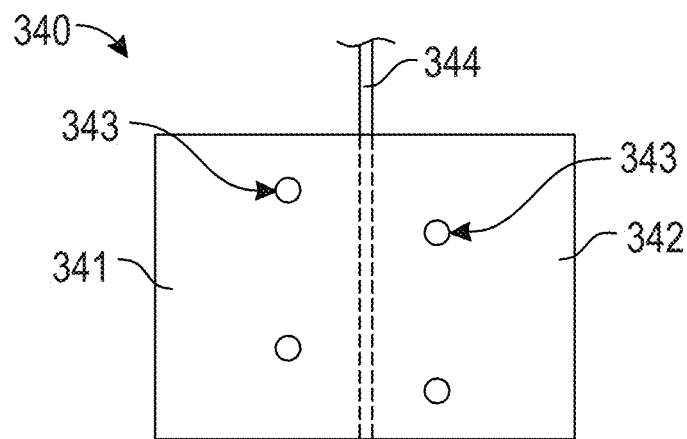

FIGS. 6B-6D schematically depict an example of a pledget as described elsewhere herein. FIG. 6B schematically depicts a pledget 340 formed by affixing a distal end (shown in dashed lines) of the suture 344 between two flat sheets, such that the sheets for left and right wings 341, 342. FIG. 6C shows a cross-section of the pledget 340 along the axis of B-B illustrated in FIG. 6B. In some embodiments, the suture 344 may be inserted between two sheets (e.g., substantially down the middle of the sheets) and pressed and/or laminated to join the three components together (e.g., under heat and/or pressure). At least one of the layers may be partially sintered. The suture 344 may be flattened and/or densified to improve resistance to suture tear out. The sheets may be flat polytetrafluoroethylene (PTFE) sheets (e.g., thin uncured expanded PTFE (ePTFE) sheets) or any other suitable material. In some implementations, the leaflet suture 344 may be disposed between the sheets in alternative configurations, such as a zig-zag or s-shaped configuration. FIG. 6D shows the pledget 340 of FIG. 6B comprising a plurality of apertures 343 through which the proximal tail end of the suture 344 may be threaded through.

In some embodiments, one or more apertures 343 may be formed through the pledget, in various configurations, to form a collapsible structure, as described elsewhere herein, which is configured to anchor the suture 344 against the mitral leaflet. FIG. 6D shows apertures 343 alternating around opposing sides of the suture 344. In some embodiments, the apertures 343 may be formed on the same side of the suture 344 (e.g., in wing 341 or wing 342). In some embodiments, the apertures 343 may be formed through the suture 344. The apertures 343 may be aligned along a center of the pledget 340. The apertures 343 may be aligned along the length of the suture 344 (e.g., may form a straight line). The suture 344 may be at least partially flattened between the two opposing sheets, which may facilitate the placement of apertures 343 through the suture 344. Various combinations of apertures 343, including the positioning described above, may be used.

The pledget 340 may be formed such that the wings 341, 342 are approximately the same size or they may be formed to be different sizes. Upon proximal retraction of the leaflet suture 344, the pledget 340 may be folded to assume an accordion-like conformation, as depicted in FIG. 6A. The pledget 340 may assume a conformation comprising a substantially planar proximal surface which is approximately perpendicular to the longitudinal axis of the leaflet suture 344. This conformation may facilitate anchoring the suture 344 in the leaflet. Upon anchoring the leaflet suture 344 in the leaflet, the leaflet anchor delivery subsystem 340 may be withdrawn from the delivery catheter 100. The leaflet anchor delivery components may be proximally retracted over a proximal end of the suture 344, which may remain extending through the delivery catheter 100 to the leaflet anchor 340, alongside the ventricular anchor suture 74.

Figure 9:
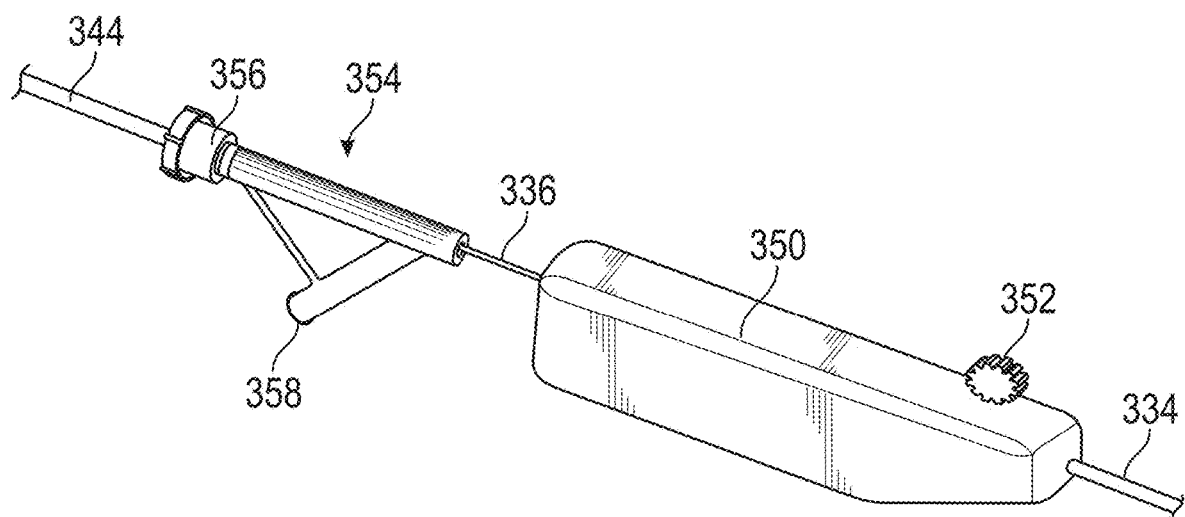
FIG. 9 illustrates a perspective view of a proximal end of the leaflet anchor delivery subsystem.

FIGS. 8-10 illustrate various views of the leaflet anchor delivery subsystem 330 and its components. FIG. 8 depicts a perspective view of a distal end of the subsystem 330. FIG. 9 depicts a perspective view of a proximal end of the subsystem 330. FIG. 10 depicts an exploded view of the distal end of the subsystem 330.

As shown in FIGS. 8 and 10, the leaflet anchor delivery subsystem 330 may comprise an outer delivery tube 332. The tube 332 may optionally include a deflection zone and may be configured to be steerable by an operator such as by proximal retraction of one or two or more pull wires (not shown) along various sides of the flex tube 332. The operator may control the flexion of the flex tube via a knob 352 or lever or other actuation mechanism positioned on a handle 350 at the proximal end of the leaflet anchor delivery subsystem 330, as shown in FIG. 9.

An internal tubular shaft or needle 336 terminating at a distal end with a needle point 338 may extend through the delivery tube 332. The internal needle 336 may comprise a hypotube, extrusion or braided tube or catheter which is flexible enough to conform to the shape of the optional flex tube 332. A needle tip 338 may be coupled to the distal end of the internal flexible shaft 336. A flexible jacket 333 may surround the flex tube 332 and a delivery shaft 334.

The proximal end of the internal tubular shaft 336 may be connected to a needle handle 354, as shown in FIG. 9. The needle handle 354 may comprise a hemostasis valve 356. The leaflet suture 344 may be inserted through valve 356. Valve 356 may be a tuohy-borst valve. The needle handle 354 may include additional ports 358 for accessing the lumen of the internal flexible shaft 336. The needle handle 354 may be positioned proximally to the handle 350 such that the internal flexible shaft 336 extends through the handle 350 and into the lumen of the delivery shaft 334. The handle 350 may comprise a hemostasis valve for receiving the internal flexible shaft 336 and sealing the internal components of the handle, including the opening to the delivery shaft 334, from the ambient environment.

The needle tip 338 may be extendable and retractable by extending the needle handle 354 toward the handle 350 or retracting the needle handle 354 from the handle 350, respectively. Distal advance of the needle 336 may be accomplished by manually advancing the handle 354. Alternatively, the distal advance of the needle may be assisted by a mechanical or electromechanical mechanism to produce a relatively high velocity, low stroke length distal advance.

Exertion of pressure on the leaflet when the needle tip 338 is extended distally beyond the tube 332 may cause the needle tip 338 to puncture the leaflet such that the needle tip 338 may extend through to the opposite side (e.g., the atrial side) of the leaflet, as shown in FIG. 4. This pressure may be exerted by extending the needle tip 338 and/or retracting the entire delivery device 330 in a proximal direction with the needle tip 338 in an extended position.

The ventricular anchor suture 74 and the leaflet anchor suture 344 may be coupled together in a tensioned fashion to form the neo chordae implant or to join two sections of the neo chordae implant together, such that the neo chordae extends between the ventricular anchor 302 and the leaflet anchor 340 across the atrial side of the coaptive edge of the leaflet. The overall length of the neo chordae may be adjusted by proximal traction of one or both sutures 74, 344 prior to engaging the suture lock 376 such that an appropriate tension is applied to the leaflet, with the tension subsequently maintained by the ventricular anchor 302. The sutures 74, 344 may remain extending proximally through the delivery catheter 100 to a location outside the body. In some embodiments, the proximal ends of the suture 74, 344 may be fed into a handle or proximal portion of a suture lock delivery system 370 to facilitate placement of the suture lock and cutting of the sutures 74, 344. In some embodiments, the proximal ends may remain free or coupled or secured by other means.

Figure 11:
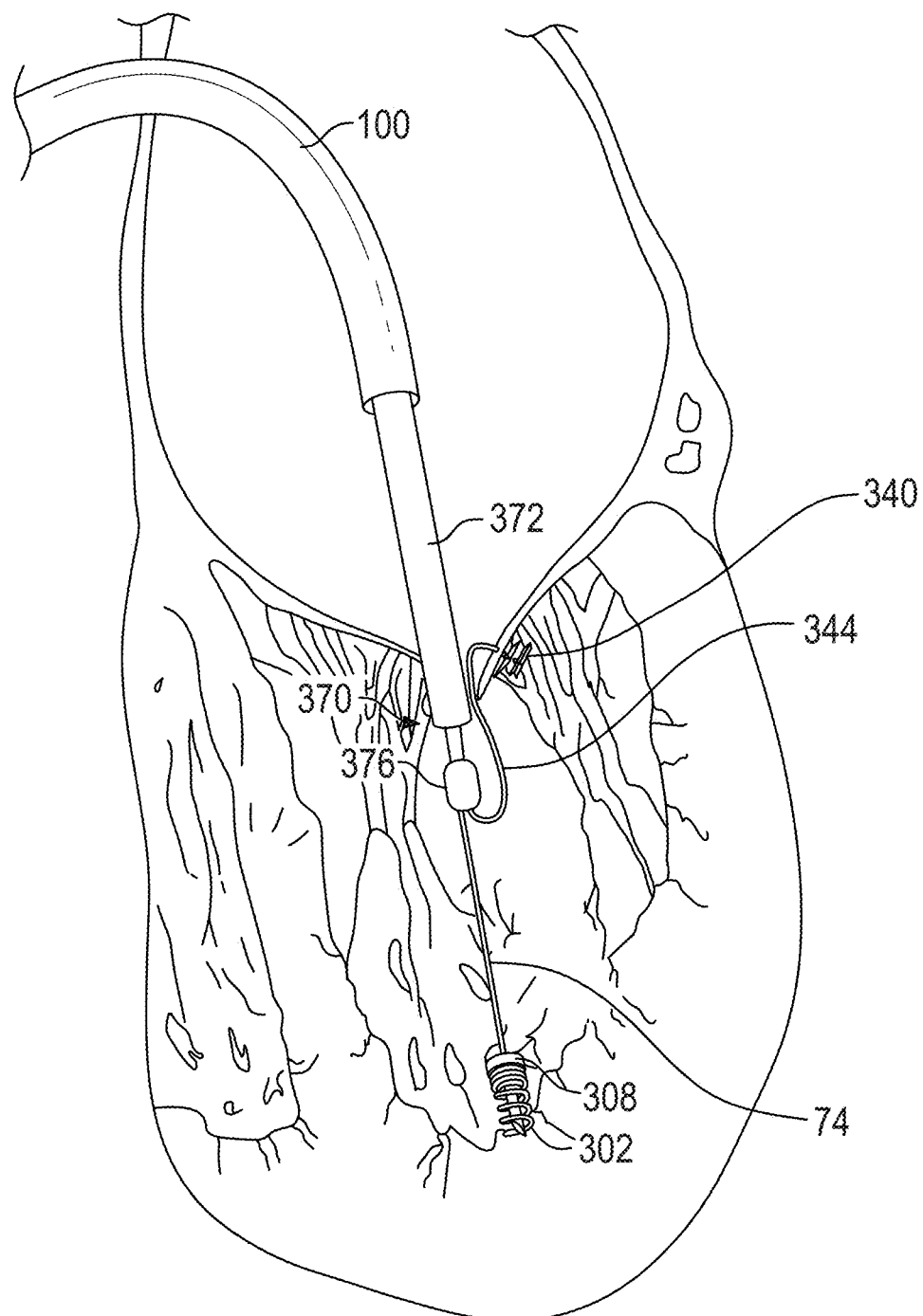
FIG. 11 depicts advancing a suture lock via a suture lock delivery subsystem over the leaflet anchor suture and ventricular anchor suture to connect the leaflet anchor to the ventricular anchor.
Figure 12:
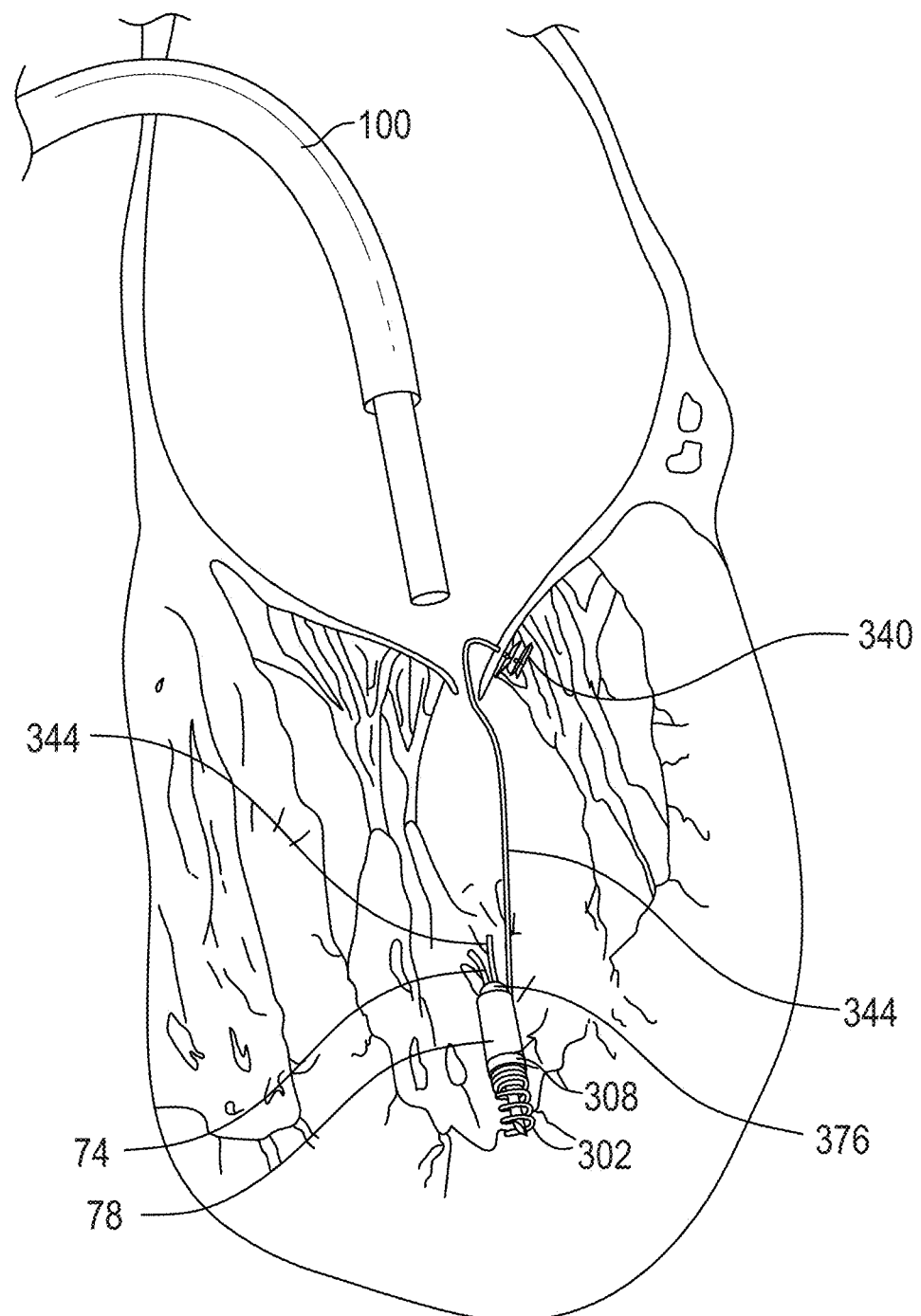
FIG. 12 depicts the suture lock in a locked position after the tension has been adjusted and the suture tails having been severed.

FIG. 11 depicts the advancement of suture lock 376 over the ventricular anchor suture 74 and the leaflet suture 344. The suture lock delivery subsystem 370 may be advanced through the delivery catheter 100 and a tubular pusher catheter 372 may push a suture lock 376 along the distal direction of the sutures 74, 344. Once the suture lock 376 has reached the ventricle, it can continue to be pushed along the ventricle suture 74 with proximal traction on the suture 74 and while allowing the leaflet suture 344 to feed distally through the catheter if needed for the suture lock 376 to advance distally to the ventricular anchor. As discussed further below, FIG. 12 illustrates the final construct with the leaflet anchor and ventricular anchors tethered together to form an artificial chordae. The proximal tails of the two sutures has been severed and catheter proximally retracted from the ventricle through the mitral valve.

Figure 13:
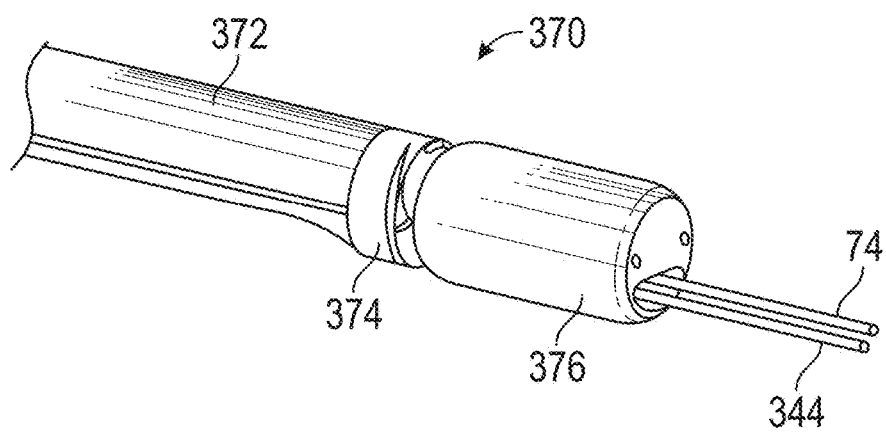
FIG. 13 depicts a perspective view of a distal end of the suture lock delivery subsystem.
Figure 14:
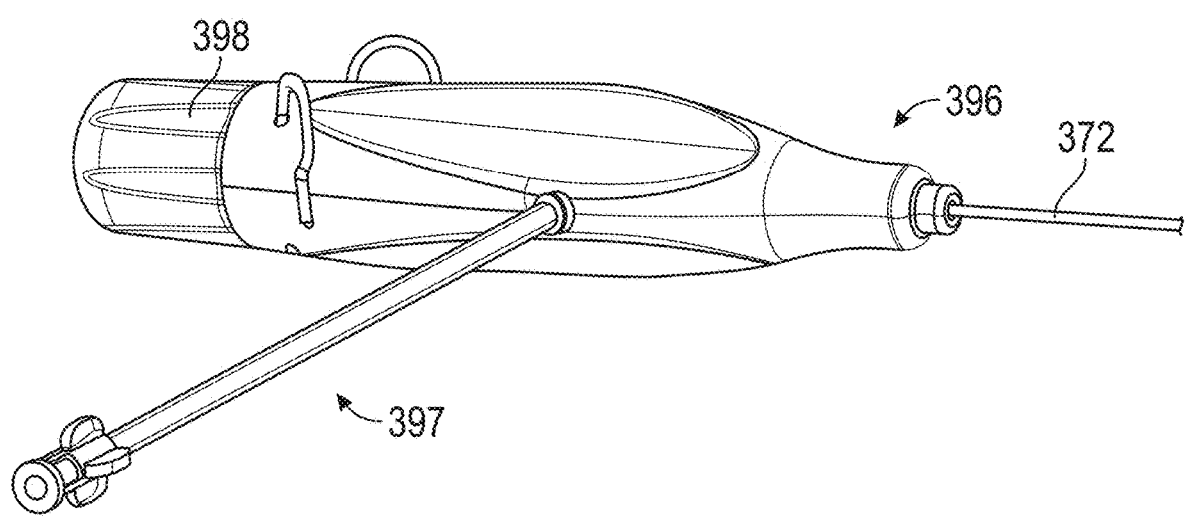
FIG. 14 depicts a perspective view of a proximal end of the suture lock delivery subsystem.
Figure 15:
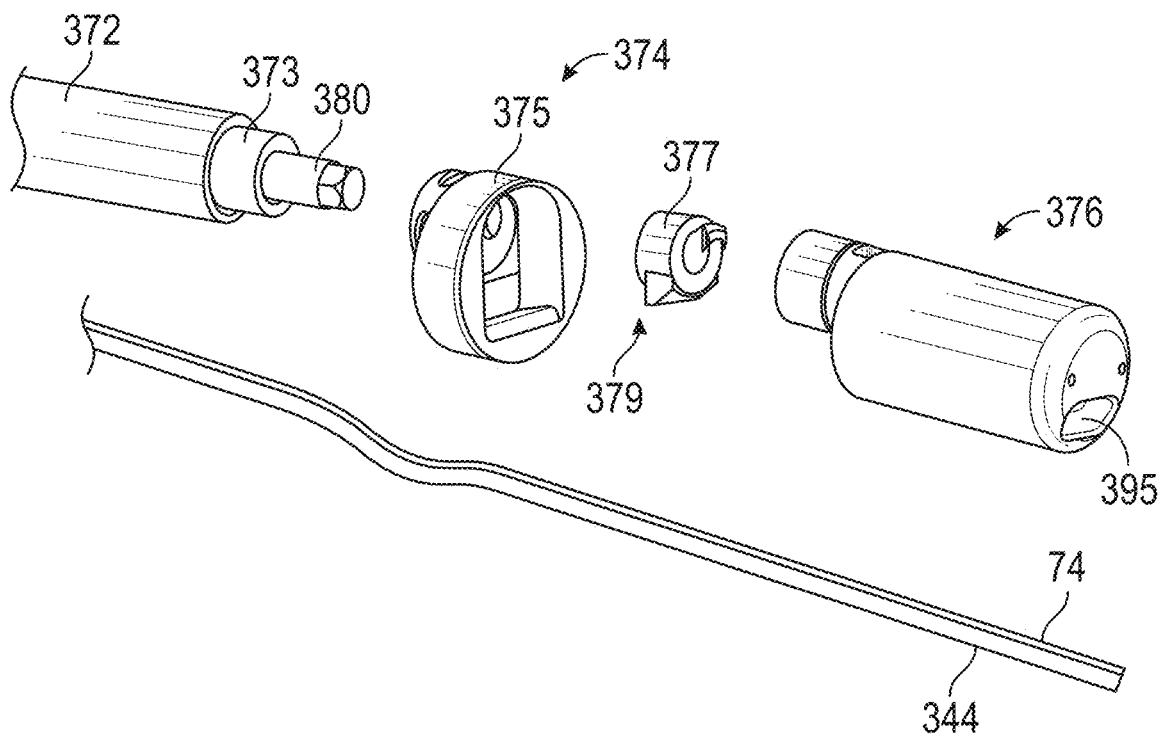
FIG. 15 depicts a partially exploded view of the distal end of the suture lock delivery subsystem.
Figure 16:
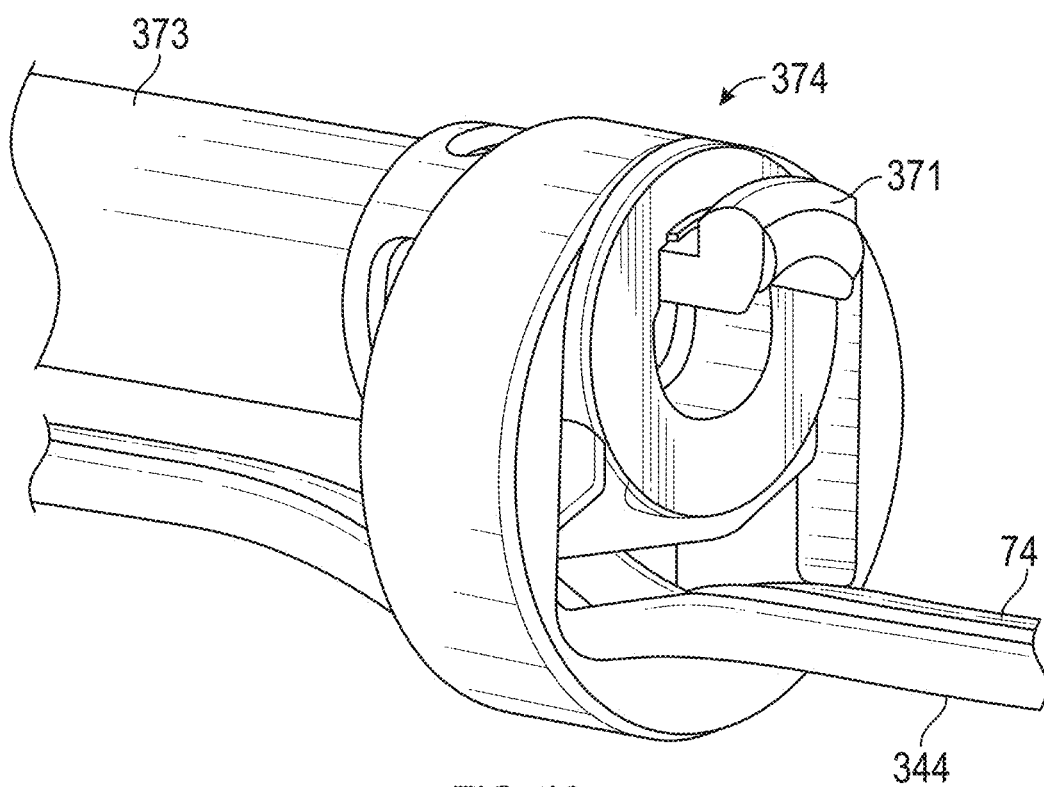
FIG. 16 depicts a perspective view of a distal end of a suture cutting assembly.
Figure 17:
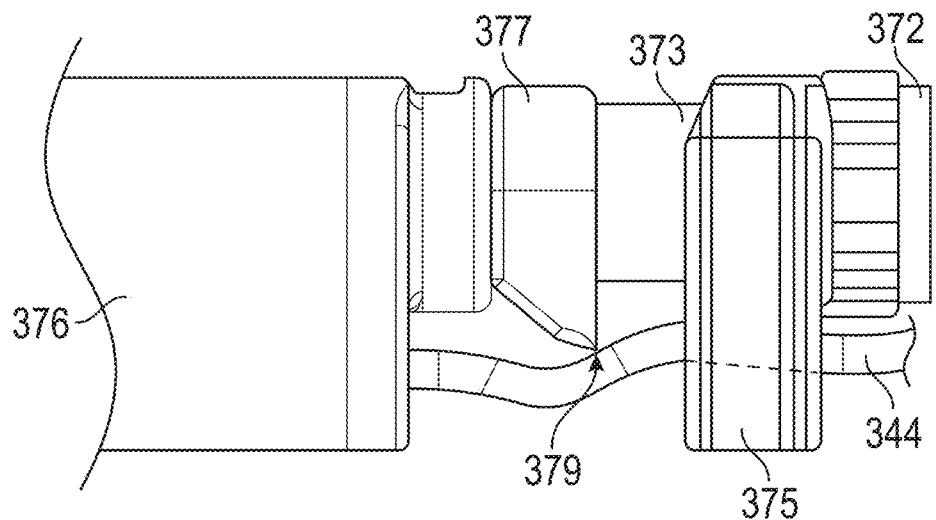
FIG. 17 depicts a side view of a cutting assembly portion of the suture lock delivery subsystem in a configuration where the cutting head is not yet advanced for holding the sutures prior to being severed.
Figure 18:
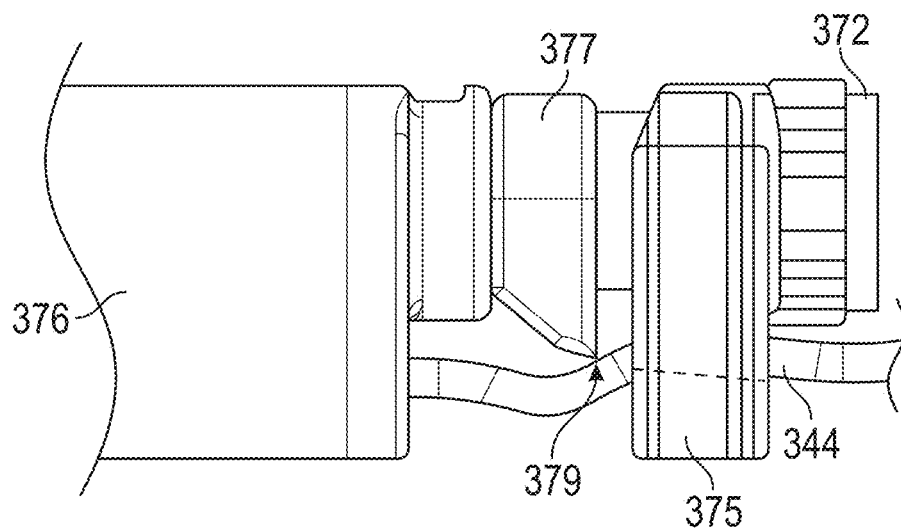
FIG. 18 depicts a side view of the cutting assembly portion of the suture lock delivery subsystem in a configuration where the cutting head has been advanced for severing the sutures.
Figure 19:
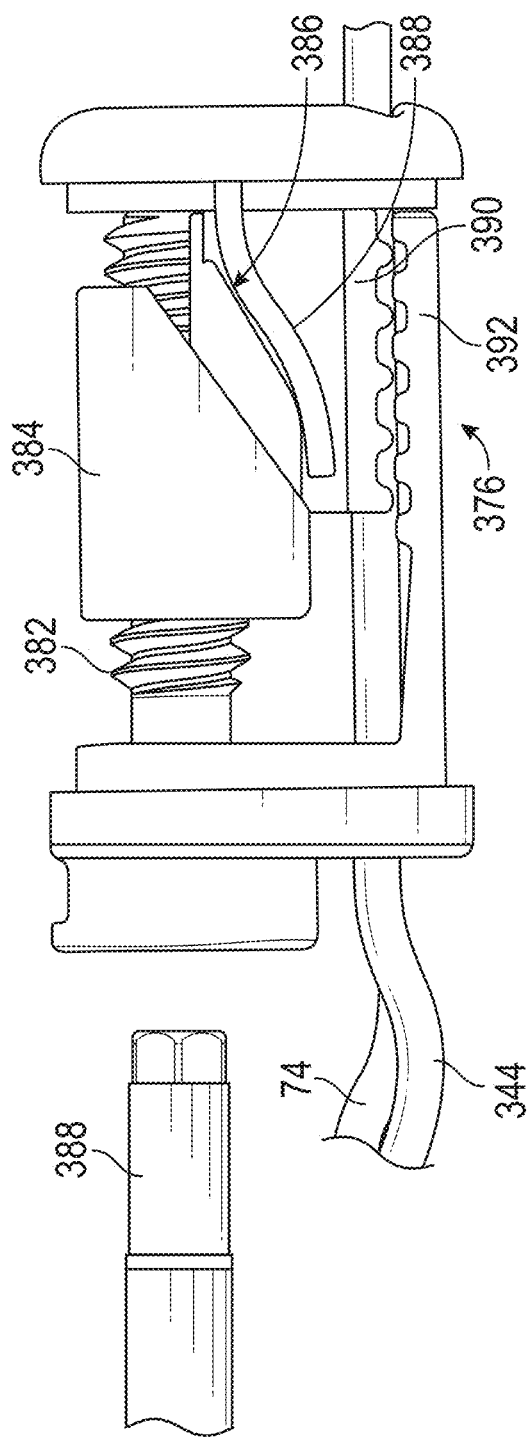
FIG. 19 depicts a side view of a suture lock and a distal end of a torque driver configured to engage the suture lock.
Figure 20:
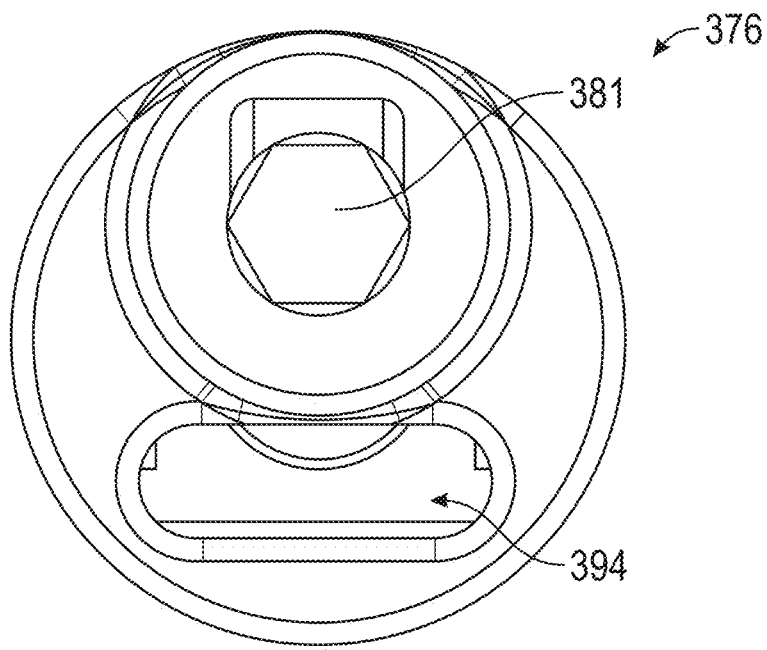
FIG. 20 depicts a proximal end view of a suture lock.
Figure 21:
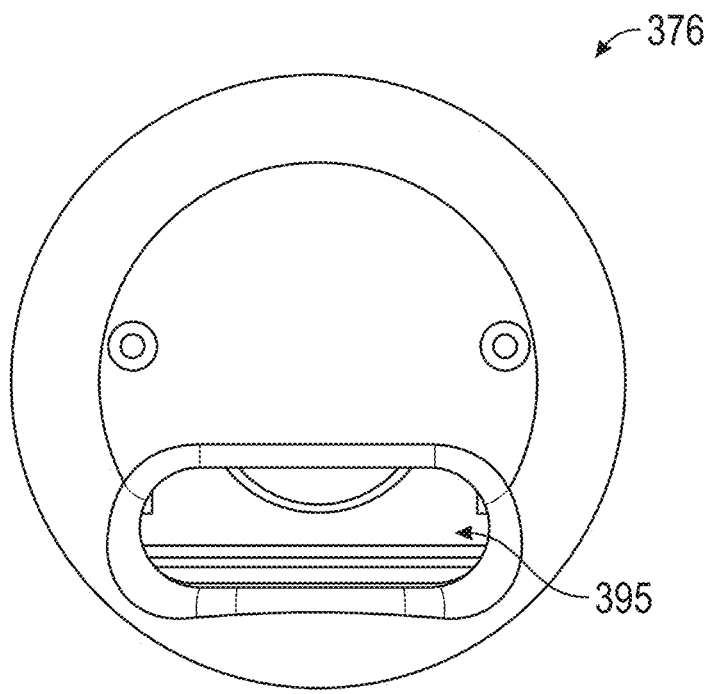
FIG. 21 depicts a distal end of view of a suture lock.

FIGS. 13-14 illustrate various views of the suture lock delivery subsystem 370 and its components. FIG. 13 depicts a perspective view of a distal end of the subsystem 370. FIG. 14 depicts a perspective view of a proximal end of the subsystem 370. FIG. 15 depicts a partially exploded view of the distal end of the subsystem 370. FIG. 16 depicts a perspective view of a distal end of a cutting assembly. FIGS. 17 and 18 depict side views of a cutting assembly portion of the subsystem 370. FIG. 19 depicts a side view of a suture lock 376 and a distal end of a torque driver 388 configured to engage the suture lock 376. FIGS. 20 and 21 depict a proximal end view and a distal end view, respectively, of the suture lock 376.

The suture lock delivery subsystem 370 may be configured to advance (e.g., slide) a suture lock 376 over both the sutures 74, 344 (or even three or four or additional sutures) securing them together. The sutures 74, 344 may each be proximally retracted relative to the suture lock 376 to tension the sutures 74, 344 and modulate the length of each suture 74, 344 between the suture lock 376 and the respective tissue anchors 302, 340. Once the tension and length of the neo chordae implant is optimized, the suture lock 376 may be locked to fix the length of the sutures 74, 344 such that the sutures 74, 344 can no longer move with respect to the suture lock 376. The sutures 74, 344 may then be severed at a point proximal to the suture lock 376. The suture 74, 344 may be cut by the same suture lock delivery subsystem 370 which delivered the suture lock 376. In other embodiments, a separate cutting device may be inserted into the delivery catheter 100 after the suture lock has been locked in place.

The suture lock allows one or two or more sutures to be advanced therethrough and adjusted, and then locked with sufficient clamping efficiency that an ePTFE suture can be prevented from slipping from the suture lock under normal use conditions (e.g., withstand tension of at least about 60% or 80% or more of the suture breaking strength, without slipping). The lock may be reopened to permit readjustment of the tension on the mitral leaflet, and retightened, until a desired result has been achieved. The tightening tool may then be removed, leaving the suture lock behind.

The suture lock 376 may be advanced along the sutures by a retainer catheter 373. The distal end of the retainer catheter 373 may be coupled to a retainer element 377 (FIG. 15). The retainer element may comprise a flange 371 or other mechanical feature configured to engage the suture lock 376. For example, the flange 371 may be inserted into a recess at a proximal end of the suture lock 376. In some embodiments, rotation of the retainer catheter 373 and/or translation substantially perpendicular to the axial direction of the retainer catheter 373 may be used to disengage the retainer catheter 373 from the suture lock 376.

The sutures 74, 344 may extend from their respective tissue anchors to pass through the suture lock 376, entering from a distal opening 395 in a distal face of the suture lock 376, shown in FIG. 21, and exiting at a proximal opening 394 to the suture path in a proximal face of the suture lock 376, shown in FIG. 20. The sutures 74, 344 may extend through a channel in a cutter head 375 proximal to the suture lock 376 and along the outside of the retainer catheter 373 and through the delivery catheter 100. The cutter head 375 may be coupled to the distal end of a cutter catheter 372. The retainer catheter 373 may extend through an internal lumen of the cutter catheter 372 such that the two catheters 372, 373 may be extendable or retractable relative to one another.

Once the sutures 74, 344 are locked (fixedly secured) within the suture lock 376, the proximal ends of the suture 74, 344 may be cut adjacent to the proximal face of the suture lock. The sutures 74, 344 may be cut by advancing the cutter catheter 372 coupled to the cutter head 375 toward the proximal face of the suture lock 376. As schematically illustrated in FIGS. 17-18, as the cutter head 375 advances along the retainer catheter 373 toward the retainer element 377, the cutter head brings the sutures 74, 344 into close proximity to a cutting blade 379 positioned on the retainer element 377. The cutter head 375 is configured to advance over the retainer element 377 in such a fashion that the channel in the cutter head 375 retaining the sutures 74, 344 becomes increasingly spatially occupied by the blade 379. As the blade 379 is forced into the channel of the cutter head 375, the blade 379 shears the sutures 74, 344. Application of proximal tension to the sutures 74, 344 may facilitate the cutting of the sutures 74, 344. In other embodiments, different actuations (e.g., rotation of a cutting catheter) can be configured to sever the sutures 74, 344.

In some implementations, more than two sutures may be employed and may be locked within the suture lock 376 and severed by the suture lock delivery subsystem 370 in the same fashion. In some embodiments, advancement of the cutter head 375 over the retainer element 377 may facilitate the disengagement of the retainer catheter 373 from the suture lock 376. For example, the cutter head 375 may advance to a distal position where it is configured to stabilize the suture lock 376, allowing the retainer catheter 373 to be axially and/or rotationally disengaged from the suture lock 376.

FIG. 19 illustrates a side view of an example of a suture lock 376 (shown with its outer casing/shell removed). The sutures may pass through the suture lock 376 from a distal end to a proximal end as described elsewhere herein. The suture lock 376 may comprise a screw 382 configured to distally advance or proximally retract a push wedge 384, depending on the direction of rotation of the screw. The screw 382 may be rotated by a torque shaft 388. The torque shaft 388 may comprise a driver head configured to mate with recess 381 (e.g., a polygonal recess or other non-circular shaped recess, as shown in FIG. 20) positioned at the proximal end of the suture lock 376 such that rotation of the torque shaft 388 causes rotation of the screw 382. The torque shaft 388 may extend through an internal lumen of the retainer catheter 373. The torque shaft 388 may be rotated at its proximal end by a knob 398 or other actuation mechanism positioned at a proximal end of the subsystem handle 396. The handle 396 may include a hemostasis valve 397. In some implementations, the sutures 311, 344 may pass through the hemostasis valve 397.

Advancement of the push wedge 384 by the torque shaft 388 may cause a ramp or angled surface 386 to gradually compress one or more springs, such as spring pins 388. The springs bias the clamp upward to open the suture path until forced closure by rotation of the torque shaft 388. Compression of the one or more springs 388 may force a clamp 390 downward on the sutures 311, 344, compressing the sutures 311, 344 between two opposing surfaces. In some embodiments, the clamp 390 and the opposing surface 392 may have notched surfaces configured to mate with each other at discrete increments. The mated notched surfaces may provide enhanced friction and in some implementations mechanical interference for retention of the sutures 311, 344 between the opposing surfaces such that they cannot be withdrawn, either proximally or distally, from the suture lock 376. In some embodiments, the tightening may be reversible by rotating the torque shaft in an opposite direction.

Once the suture lock is properly positioned over the sutures 74, 344 and locked into place, the sutures 74, 344 may be severed as described elsewhere herein. FIG. 12 depicts the retraction of the suture lock delivery subsystem 370 after the sutures 74, 344 have been cut. Once the suture lock delivery subsystem 370 has been removed from the delivery catheter 100, the delivery catheter 100 may be withdrawn from the body.

Although this disclosure describes certain embodiments and examples, many aspects of the above-described systems and methods may be combined differently and/or modified to form still further embodiments or acceptable examples. All such modifications and variations are intended to be included herein within the scope of this disclosure. Indeed, a wide variety of designs and approaches are possible and are within the scope of this disclosure.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

The disclosure herein of any particular feature, aspect, method, property, characteristic, quality, attribute, element, or the like in connection with various embodiments can be used in all other embodiments set forth herein. Also, any methods described herein may be practiced using any device suitable for performing the recited steps.

Moreover, while components and operations may be depicted in the drawings or described in the specification in a particular arrangement or order, such components and operations need not be arranged and performed in the particular arrangement and order shown, nor in sequential order, nor include all of the components and operations, to achieve desirable results. Other components and operations that are not depicted or described can be incorporated in the embodiments and examples. For example, one or more additional operations can be performed before, after, simultaneously, or between any of the described operations. Further, the operations may be rearranged or reordered in other implementations. Also, the separation of various system components in the implementations described above should not be understood as requiring such separation in all implementations, and it should be understood that the described components and systems can generally be integrated together in a single product or packaged into multiple products.

In summary, various illustrative embodiments and examples are described herein. Although the systems and methods have been disclosed in the context of those embodiments and examples, this disclosure extends beyond the specifically disclosed embodiments to other alternative embodiments and/or other uses of the embodiments, as well as to certain modifications and equivalents thereof. This disclosure expressly contemplates that various features and aspects of the disclosed embodiments can be combined with, or substituted for, one another. Accordingly, the scope of this disclosure should not be limited by the particular disclosed embodiments described above, but should be determined only by a fair reading of the claims that follow as well as their full scope of equivalents.

What is claimed is:

1. A leaflet anchor deployment system, comprising:
   a catheter having a proximal end and a distal end;
   a leaflet connector positioned on a distal end of the catheter;
   a needle advanceable through the leaflet connector, the needle including a radially enlargeable leaflet anchor preloaded therein and having a suture extending proximally through the catheter; and
   wherein the leaflet connector comprises a sharpened tip for piercing the leaflet and wherein the leaflet connector comprises a helical tissue anchor, the leaflet anchor is enlargeable from an axially elongated configuration within the needle to an axially shortened and radially enlarged configuration against the leaflet and wherein the leaflet anchor comprises a fabric pledget having a plurality of transverse folds forming a plurality of stacked panels when in the axially shortened configuration and wherein the pledget comprises two wings which may be rolled around a longitudinal axis of the pledget to produce a reduced cross section conformation.

2. The system of claim 1, further comprising a push wire, for pushing the leaflet anchor out of the needle.

3. The system of claim 1 wherein conversion to the axially shortened and radially enlarged configuration is accomplished by proximal retraction of a leaflet anchor suture.

4. The system of claim 1, wherein the pledget comprises ePTFE.

5. A leaflet anchor deployment system, comprising:
   a catheter having a proximal end and a distal end;
   a leaflet connector positioned on a distal end of the catheter;
   a needle advanceable through the leaflet connector, the needle including a radially enlargeable leaflet anchor preloaded therein and having a suture extending proximally through the catheter; and
   wherein the leaflet connector comprises a sharpened tip for piercing the leaflet and wherein the leaflet connector comprises a helical tissue anchor, the leaflet anchor is enlargeable from an axially elongated configuration within the needle to an axially shortened and radially enlarged configuration against the leaflet and wherein the leaflet anchor comprises a fabric pledget having a plurality of transverse folds forming a plurality of stacked panels when in the axially shortened configuration;

wherein the pledget comprises two sheets having a distal section of leaflet anchor suture bonded therebetween.

6. The system of claim 5 wherein the distal section of leaflet anchor suture is flattened between the two sheets.

7. The system of claim 5 wherein the two sheets comprise a plurality of apertures and the leaflet anchor suture extends slidably through the apertures.

8. A leaflet anchor delivery subsystem, comprising:
an elongate flexible tubular body, having a proximal end, a distal end, a central lumen, and a handle at the proximal end of the tubular body, wherein the tubular body axially movably extends through an outer delivery tube;
a deployment needle axially movably advanceable through the central lumen;
a foldable pledget leaflet anchor carried within the deployment needle; and
a leaflet connector carried by the distal end of the tubular body, wherein the deployment needle comprises an elongate flexible shaft which extends proximally to a needle handle,
wherein the needle handle comprises a hemostasis valve.

9. The leaflet anchor delivery subsystem of claim 8, wherein the leaflet connector comprises a helical element.

10. The leaflet anchor delivery subsystem of claim 9, wherein the deployment needle is axially extendable through the helical element.

11. The leaflet anchor delivery subsystem of claim 8, wherein the outer delivery tube comprises a deflection zone and at least one pull wire.

12. The leaflet anchor delivery subsystem of claim 8 wherein the leaflet anchor comprises a pledget.

13. The leaflet anchor delivery subsystem of claim 12, wherein the pledget comprises a plurality of transverse folds forming a plurality of stacked panels when in an axially shortened configuration.

14. The leaflet anchor delivery subsystem of claim of claim 13, wherein the pledget comprises two sheets having a distal section of a leaflet anchor suture bonded therebetween.

15. The leaflet anchor delivery subsystem of claim 13 wherein the distal section of leaflet anchor suture is flattened between the two sheets.

16. The leaflet anchor delivery subsystem of claim of claim 13, further comprising a push wire, for pushing the leaflet anchor out of the needle.

17. The leaflet anchor delivery subsystem of claim of claim 16 wherein the pledget can be converted from the axially shortened and radially enlarged by proximal retraction of a leaflet anchor.

* * * * *

UNITED STATES PATENT AND TRADEMARK OFFICE
CERTIFICATE OF CORRECTION

PATENT NO. : 10,660,753 B2  
APPLICATION NO. : 16/509230  
DATED : May 26, 2020  
INVENTOR(S) : Trung Ho Pham It is certified that error appears in the above-identified patent and that said Letters Patent is hereby corrected as shown below:

On the Title Page

Column 1, Item (73), under Assignee, Line 1, delete "Techologies" and insert --Technologies--.

On Page 3, Column 2, Item (56), under Other Publications, Line 2, delete "stardardized" and insert --standardized--.

In the Specification

In Column 4, Line 26, delete "transceptal" and insert --transseptal--.

In Column 5, Line 20, delete "(the" and insert --the--.

In Column 5, Line 37, delete "transceptal" and insert --transseptal--.

In Column 15, Lines 51-52, delete "sub combination." and insert --subcombination.--.

In the Claims

In Column 16, Line 39, Claim 1, delete "leaflet" and insert --leaflet;--.

In Column 16, Line 67, Claim 5, delete "leaflet" and insert --leaflet;--.

In Column 18, Lines 14-15, Claim 14, delete "of claim of claim" and insert --of claim--.

In Column 18, Lines 21-22, Claim 16, delete "of claim of claim" and insert --of claim--.

In Column 18, Lines 23-24, Claim 17, delete "of claim of claim" and insert --of claim--.

Signed and Sealed this  
Twenty-fifth Day of August, 2020

Andrei Iancu  
*Director of the United States Patent and Trademark Office*